US010982201B2

(12) United States Patent
Schriemer et al.

(10) Patent No.: US 10,982,201 B2
(45) Date of Patent: *Apr. 20, 2021

(54) TREATMENT OF GLUTEN INTOLERANCE AND RELATED CONDITIONS

(71) Applicant: Codexis, Inc., Redwood City, CA (US)

(72) Inventors: David C. Schriemer, Chestermere (CA); Petr Man, Prague (CZ); Hynek Mrazek, Prague (CZ); Martial Rey, Calgary (CA)

(73) Assignee: Codexis, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/357,191

(22) Filed: Mar. 18, 2019

(65) Prior Publication Data

US 2020/0040322 A1 Feb. 6, 2020

Related U.S. Application Data

(60) Continuation of application No. 15/209,681, filed on Jul. 13, 2016, now Pat. No. 10,266,818, which is a continuation of application No. 14/620,066, filed on Feb. 11, 2015, now abandoned, which is a division of application No. 13/843,369, filed on Mar. 15, 2013, now Pat. No. 9,005,610.

(60) Provisional application No. 61/797,040, filed on Nov. 27, 2012, provisional application No. 61/729,210, filed on Nov. 21, 2012.

(51) Int. Cl.
*C12N 9/50* (2006.01)
*A61K 38/48* (2006.01)
*A23L 29/00* (2016.01)
*A23L 33/10* (2016.01)
*A23L 33/105* (2016.01)
*A61K 38/00* (2006.01)

(52) U.S. Cl.
CPC .............. *C12N 9/63* (2013.01); *A23L 29/06* (2016.08); *A23L 33/10* (2016.08); *A23L 33/105* (2016.08); *A61K 38/488* (2013.01); *C12Y 304/23012* (2013.01); *A23V 2002/00* (2013.01); *A61K 38/00* (2013.01)

(58) Field of Classification Search
None
See application file for complete search history.

(56) References Cited

U.S. PATENT DOCUMENTS

| 5,618,564 | A  | * | 4/1997  | Kimura  | A61K 33/245 424/653 |
|---|---|---|---|---|---|
| 7,320,788 | B2 | * | 1/2008  | Shan    | A61P 17/04 424/94.6 |
| 2010/0322912 | A1 | * | 12/2010 | Khosla  | A61K 38/4813 424/94.2 |
| 2012/0225050 | A1 | * | 9/2012  | Knight  | A23K 10/12 424/94.64 |

OTHER PUBLICATIONS

Athauda SBP et al. Enzymatic and structural characterization of nepenthesin, a unique member of a novel subfamily of aspartic proteinases. 2004. Biochem J. 381, 295-306. (Year: 2004).*
GenBank BAF98915.1. GenBank 2008, p. 1-2. (Year: 2008).*
GenBank AB114914.1. GenBank 2004, p. 1-2. (Year: 2004).*
GenBank AFV26025.1. GenBank 2012, p. 1-2. (Year: 2012).*
GenBank AB114915.1. GenBank 2004, p. 1-2. (Year: 2004).*

* cited by examiner

*Primary Examiner* — Paul J Holland
(74) *Attorney, Agent, or Firm* — Mintz, Levin, Cohn, Ferris, Glovsky and Popeo, P.C.

(57) ABSTRACT

Provided herein are compositions, foods comprising nepenthesin or a derivative thereof and methods of using nepenthesin or a derivative thereof for modulating gluten intolerance and related conditions, such as celiac disease. Further provided herein are pharmaceutical compositions comprising nepenthesin or a derivative thereof and methods of using nepenthesin or a derivative thereof to treat bacterial infections of the gastrointestinal tract, such as *C. difficile* or *H. pylori*. Further provided herein are compositions comprising recombinant nepenthesin I or nepenthesin II, or homologous proteins, and methods for making the same.

21 Claims, 14 Drawing Sheets

Specification includes a Sequence Listing.

A
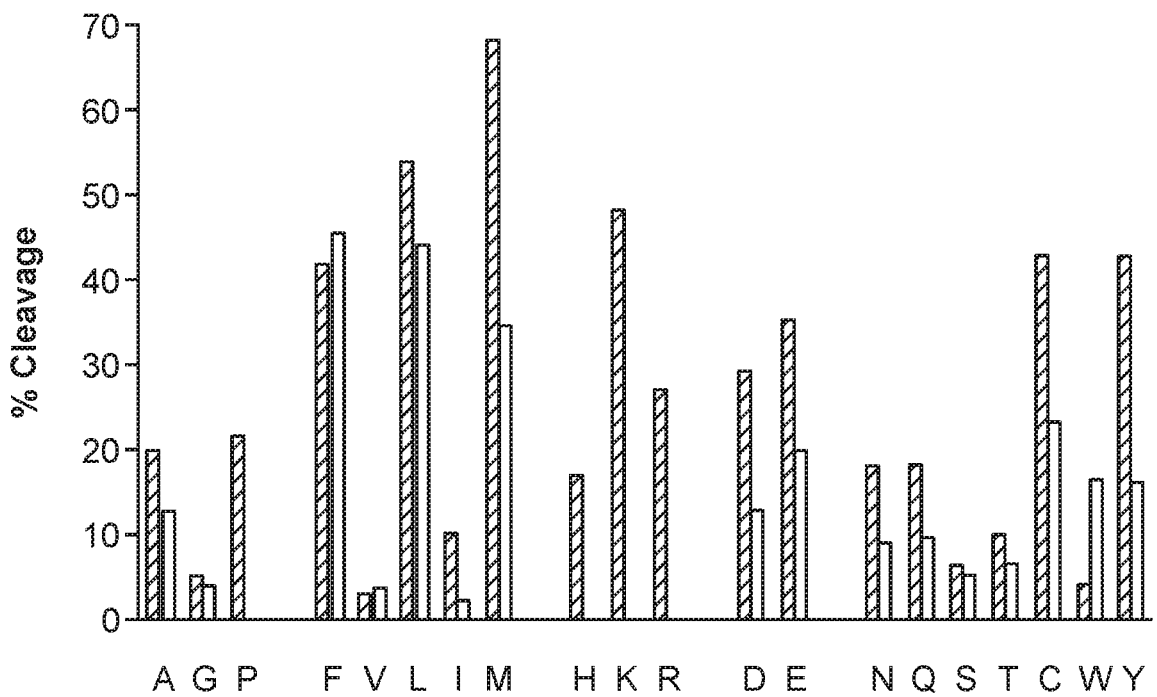
B
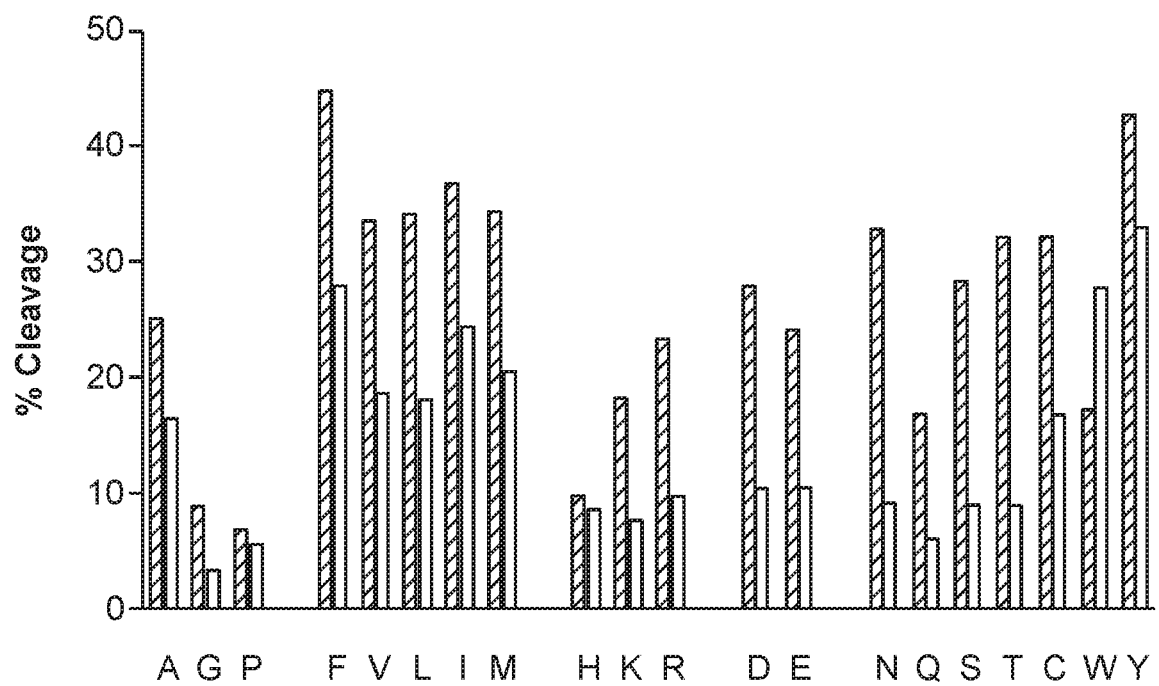
FIG. 1

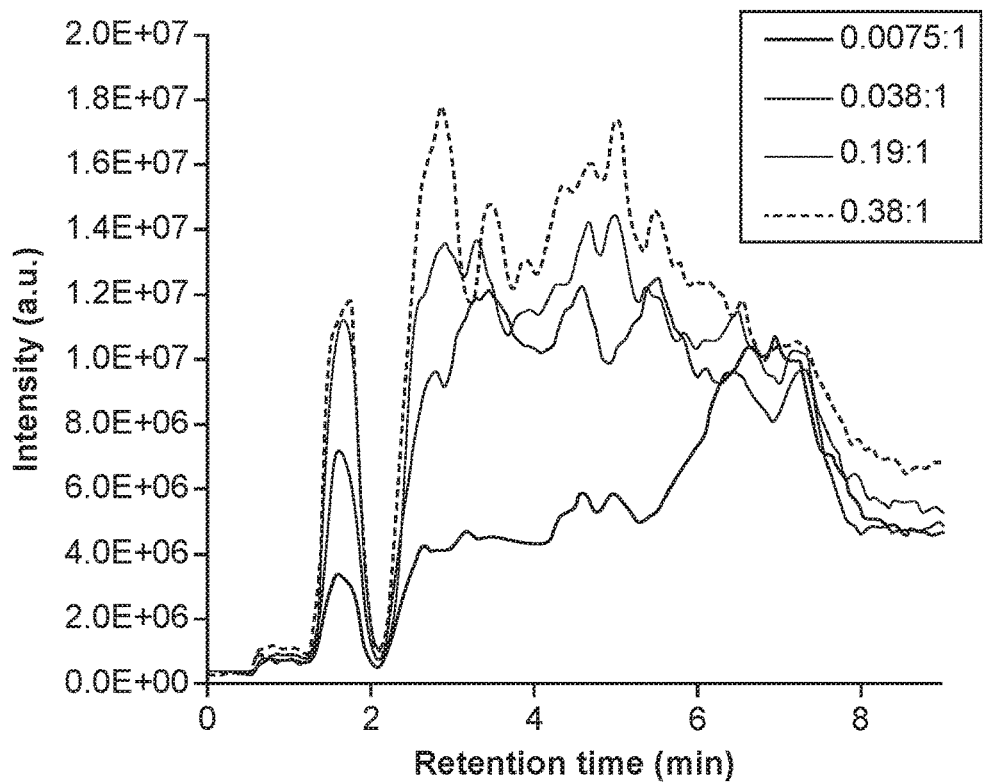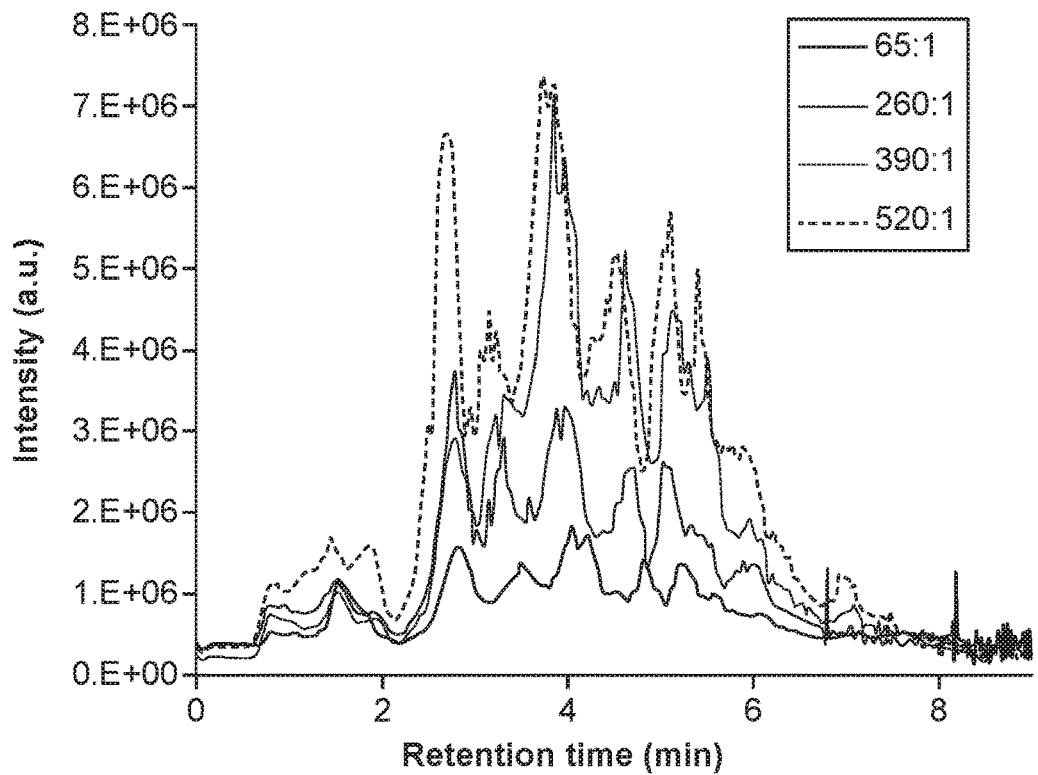
FIG. 4

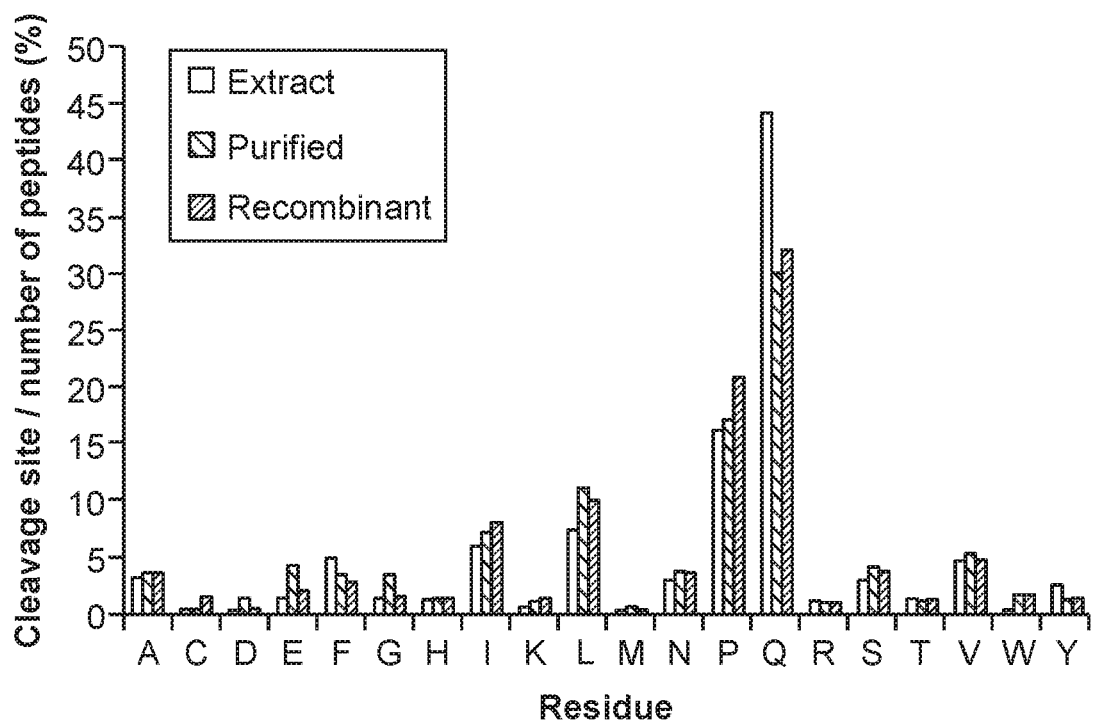
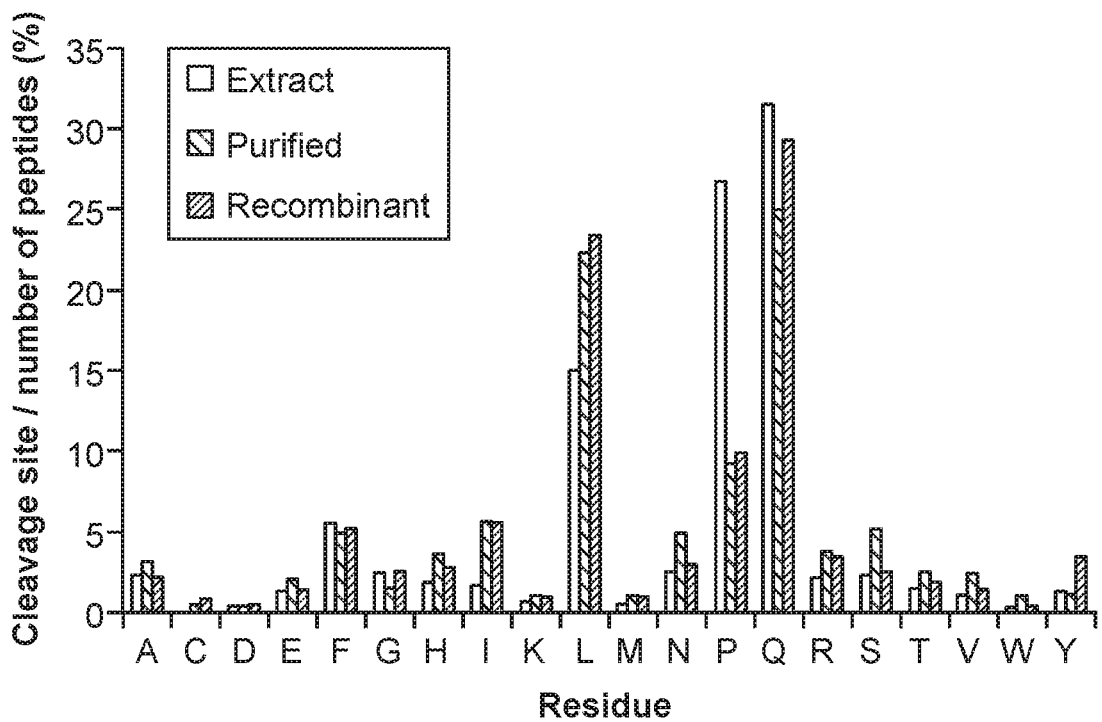
FIG. 8

```
N. mirabilis nep I   ------------------------MASSLYSFLLALSIVVIFVAPTHSTSR-TALNHHHEPKVAG----FQIMLEHVDSGKNLTKFELLERAVERGSRRLQR-------LEA
N. alata nep I       ------------------------MASSLYSFLLALSIVVIFVAPTHSTSR-TALNHHHEPKVAG----FQIMLEHVDSGKNLTKFELLERAVERGSRRLQR-------LEA
N. gracilis nep I    ------------------------MASSLYSFLLALSIVVIFVAPTHSTSR-TALNHRHEAKVTG----FQIMLEHVDSGKNLTKFQLLERAIERGSRRLQR-------LEA
N. mirabilis nep II  ------------------------MASPLHSVVLGLAIVSAIVAPTSSTSRGTLLHHGQKRPQPG----LRVVLEQVDSGMNLTKYELIKRAIKRGERRMRS-------INA
N. gracilis nep II   ------------------------MASPLYSVVLGLAIVSAIVAPTSSTSRGTLLHHGQKRPQPG----LRVDLEQVDSGKNLTKYELIKRAIKRGERRMRS-------INA
Z. mays nep I        ------------------------MAFHSCTIIPASHHSSMSSSTSQMASLAVLVFLVVCATLASGAASVRVGLTRIHSDPDTTAPQFVRDALRRDMHRQRSRSFGRDRDRE
O. sativa nep I      --------------------------------------------------MRGVSVVLVLIACWLCGCPVAGEAAFAG---DIRVDLTHVDAGKELPKRELIRRAMQRSKARAALSVRNGGF
O. sativa nep II     ------------------------MADRITVLAIALLVLILSPQMAVQGKPAAGNTASPRPKQQLGNFFKKHGSDIAGLFPRHRNGGSSGSYSGQAVPAD
Z. mays nep II       MAMMACNNTRPRKLSLPCRTRTFQALILSTAVFLAASTAVVGKEPQPPSSSGGCHYRFELTHVDANLNLTSDELMRRAYDRSRLRAAS-------L N. mirabilis nep I   MLNGPSGVETPVYAGD-----GEYLMNLSIG--TPAQPFSAIMDTGSDLIWTQCQPC-TQCFNQSTPIFNP-----QGSSSFSTLPCSSQLCQALQSPT
N. alata nep I       MLNGPSGVETPVYAGD-----GEYLMNLSIG--TPAQPFSAIMDTGSDLIWTQCQPC-TQCFNQSTPIFNP-----QGSSSFSTLPCSSQLCQALQSPT
N. gracilis nep I    MLNGPSGVETSVYAGD-----GEYLMNLSIG--TPAQPFSAIMDTGSDLIWTQCQPC-TQCFNQSTPIFNP-----QGSSSFSTLPCSSQLCQALSSPT
N. mirabilis nep II  MLQSSSGIETPVYAGS-----GEYLMNVAIG--TPASSLSAIMDTGSDLIWTQCEPC-TQCFSQPTPIFNP-----QDSSSFSTLPCESQYCQDLPSES
N. gracilis nep II   MLQSSSGIETPVYAGD-----GEYLMNVAIG--TPDSSLSAIMDTGSDLIWTQCEPC-TQCFSQPTPIFNP-----QDSSSFSTLPCESQYCQDLPSET
Z. mays nep I        LAESDGRTSTTVSARTRKDLPNGGEYLMTLAIG--TPPLPYAAVADTGSDLIWTQCAPCGTQCFEQPAPLYNP----ASSTTFSVLPCNSSLSMCAGALA
O. sativa nep I      YGSIAQAREREREPGMAVRASGDLEYVLDLAVG---TPPQPITALLDTGSDLIWTQDTC-TACLRQPDPLFSP----RMSSSYEPMRCAGQLCGDILHHS
O. sativa nep II     GGENGGGQSQDPATN------TGMYVLSFSVG---TPPQVTGVLDITSDFVWMQCSACATCGADAPAATSAPPFYAFLSSTIREVRCANRGCQRLVPQT
Z. mays nep II       AAYSDGRHEGRVSIPD-----ASYIITFYLGNQRPEDNISAVDTGSDIFWTTEKECSRSKTRSMLPCCSP------KCEQRASCGCGRSELKA N. mirabilis nep I   ------VSIPNITFGCGE--NNQGFGQNGAGLVGMRGRPLSIPSQLDVTKFSYCMTPIGSS---
N. alata nep I       ------VSIPNITFGCGE--NNQGFGQNGAGLVGMGRGPLSLPSQLDVTKFSYCMTPIGSS---
N. gracilis nep I    ------VSIPNITFGCGE--NNQGFGQNGAGLVGMGRGPLSLPSQLDVTKFSYCMTPIGSS---
N. mirabilis nep II  ----CYN-DCQYTYGYGDSSTQGYMATETFFET---SSVPNIAFGCGE--DNQGFGQNGAGLIGMGWGPLSLPSQLGVGQFSYCMTSSGSS--
N. gracilis nep II   ----CNNNECQYTYGYGDSTTQGYMATETFFET---SSVPNIAFGCGE--DNQGFGQNGAGLIGMGWGPLSLPSQLGVGQFSYCMTSYGSS--
Z. mays nep I        GAAPPPGCACMYQTYGTG-WTAGVQGSEITFFGSSA----ADQARVPGVAFGCSN--ASSSDWNG-SAGLVGLGRGSLSLVSQLGAGRFSYCLTPFQDTN
O. sativa nep I      ---CVRPDTCTYRYSYGDGTTTLGYYATERFTFASSS----GETQSVP-LGFGCGT-MNVG-SLNNASGIVFGRDPLSLVSQLSIRRFSYCLTPYASS-
O. sativa nep II     CSADDSPCGYSVVGGAANTTAGLLAVDAFAFAT------VRADGVIFGCAV-ATEG---DIGGVIGLGRGELSPVSQLQIGRFSYYLAPDDAVD
Z. mays nep II       EAEKETKCTYAIIYGNANDSTAGVMYEDKLTIVAVASKAVPSSQSFKEVAIGCSTSATLKFKDPSIKGVFGLGRSATSLPRQLNFSKFSYCLSSYQEPD
```

FIG. 9

```
N. mirabilis nep I    TSSTLLLGSLANS------VTAGSPNTTLIES---SQIPTFYYITLNGLSVGSTPLPIDPSVFKLNSNNGTGGIIIDSGTTLTYFADNAYQAVRQAFISQM
N. alata nep I        NSSTLLLGSLANS------VTAGSPNTTLIQS---SQIPTFYYITLNGLSVGSTPLPIDPSVFKLNSNNGTGGIIIDSGTTLTYFVDNAYQAVRQAFISQM
N. gracilis nep I     TPSNLLLGSLANS------VTAGSPNTTLIQS---SQIPTFYYITLNGLSVGSTRLPIDPSAFALNSNNGTGGIIIDSGTTLTYFVNNAYQSVRQEFISQI
N. mirabilis nep II   SPSTLALGSAASG------VPEGSPSTTLIHS---SLNPTYYITLQGITVGGDNLGIPSSTFQLQ-DDGTGGMIDSGTTLTYLPQDAYNAVAQAFTDQI
N. gracilis nep II    SPSTLALGSAASG------VPEGSPSTTLIHS---SLNPTYYITLQGITVGGDNLGIPSSTFQLQ-DDGTGGMIDSGTTLTYLPQDAYNAVAQAFTDQI
Z. mays nep I         STSTLLLGPSAAL------NGTGVRSTPFVASPARAPMSTYYLNLTGISLGAKALPISPGAFSLK-PDGTGGLIIDSGTTITSLANAAYQQVRAAVKSQL
O. sativa nep I       RKSTLQFGSLADVGLYDDATGPVQTTPILQS---AQNPTFYYVAFTGVTVGARRLRIPASAFALR-PDGSGGVIIDSGTALTLFPVAVLAEVVRAFRSQL
O. sativa nep II      VGSFILFLDDAKP------RTSRAVSTPLVAS---RASRSLYYVELAGIRVDGEDLAIPRGTFDLQ-ADGSGGVVLSITIPVTFLDAGAYKVVRQAMASKI
Z. mays nep II        LPSYLLLTAAPDMATGAVGGAAVATTALQP---NSDYKTLYFVHLQNISIGGTRFPAVS-----TKSGGNMFVDTGASFTRLEGTVFAKLVTELDRIM N. mirabilis nep I    N--LSVVNGS-SSGFDLCFQMPSDQSN------LQIPTFVMHFDG-GDLVLPSEN--YFISPSNGLICLAMGSSSQ-GMSIFGNIQQNLLVVYDTGNS
N. alata nep I        N--LSVVNGS-SSGFDLCFQMPSDQSN------LQIPTFVMHFDG-GDLVLPSEN--YFISPSNGLICLAMGSSSQ-GMSIFGNIQQNLLVVYDTGNS
N. gracilis nep I     N--LPVVNGS-SSGFDLCFQTPSDPSN------LQIPTFVMHFDG-GDLELPSEN--YFISPSNGLICLAMGSSSQ-GMSIFGNIQQNMLVVYDTGNS
N. mirabilis nep II   N--LSPVDES-SSGLSTCFQLPSDGST------VQVPEISMQFDG-GVLNLGEEN--VLISPAEGVICLAMGSSSQQGISIFGNIQQETQVLYDLQNL
N. gracilis nep II    N--LPTVDES-SSGLSTCFQQPSDGST------VQVPEISMQFDG-GVLNLGEQN--ILISPAEGVICLAMGSSSQLGISIFGNIQQETQVLYDLQNL
Z. mays nep I         VTTLPTVDGSDSTGLDLCFALPAPTSAP------PAVLPSMTLHFDG-ADMVLPADS--YMISGS-GWCLAMRNQTDGAMSTFGNYQQQNMHILYDVREE
O. sativa nep I       R--LPFANGS-SPDDGVCFAAPAVAAGGGRMARQVAVPRMVFHFQG-ADLDLPREN--YVLEDHRRGHLCVLLGDSGDDGATIGNFVQQDMRVVYDLERE
O. sativa nep II      E--LRAADGS-ELGLDLCYTSESLATAK------VPSMALVFAG-GAVMELEMGNYFMDSTTGLECLTILPSPAGDGSLLGSLIQVGTHMIYDISGS
Z. mays nep II        KERKYVKEQPGRNNGQICYSPPSTAADE------SSKLPDMVLHFADSANMVLPWDS--YLWKTTSKLCLAIYKSNIKGGISVLGNFQMQNTHMLLDTGNE N. mirabilis nep I    VVSFLFAQCGAS----------
N. alata nep I        VVSFLSAQCGAS----------
N. gracilis nep I     VVSFASAQCGAS----------
N. mirabilis nep II   AVSFVPTQCGAS----------
N. gracilis nep II    AVSFVPTQCGAS----------
Z. mays nep I         TLSFAPAKCSTL----------
O. sativa nep I       TLSFAPVEC-------------
O. sativa nep II      RLVFESLEQAPPPPSGSSRQSSRRSSSAPPPLTSPAVVIHLMLVVVYMFL
Z. mays nep II        KLSFVRADCSKVI---------
```

FIG. 9 (Cont.)

//TREATMENT OF GLUTEN INTOLERANCE AND RELATED CONDITIONS

CROSS-REFERENCE TO RELATED APPLICATIONS

This application is a continuation of U.S. patent application Ser. No. 15/209,681 which is a continuation of U.S. patent application Ser. No. 14/620,066, filed on Feb. 11, 2015, now abandoned, which is a divisional of U.S. patent application Ser. No. 13/843,369, filed on Mar. 15, 2013, now U.S. Pat. No. 9,005,610, which claims priority to and the benefit under 35 U.S.C. § 119(e) of U.S. Provisional Application Ser. No. 61/729,210, filed Nov. 21, 2012, and U.S. Provisional Application Ser. No. 61/797,040, filed Nov. 27, 2012. Each of the applications listed above is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Jul. 3, 2013, is named 104069-0152 SL.txt and is 40,351 bytes in size.

FIELD OF THE INVENTION

Provided herein are compositions, foods and methods for the treatment of gluten intolerance and related conditions, such as celiac disease. Further provided herein are pharmaceutical compositions comprising nepenthesin or a derivative thereof and methods of using nepenthesin or a derivative thereof to treat bacterial infections of the gastrointestinal tract, such as *C. difficile* or *H. pylori*. Further provided herein are methods for using nepenthesin or a derivative thereof in hydrogen/deuterium exchange. Further provided herein are compositions comprising recombinant nepenthesin I or nepenthesin II, or homologous proteins, and methods for making the same.

BACKGROUND OF THE INVENTION

Ingestion of wheat, barley, rye and possibly oats, which contain gluten may cause abnormal autoimmune responses, such as celiac disease, wheat allergy and dermatitis herpetiformis, in gluten intolerant individuals. Gluten is a mixture of glutamine- and proline-rich glutenin and prolamin protein molecules. Most of the individuals having the abnormal autoimmune responses express the human leukocyte antigen (HLA) DQ2 or DQ8 molecules. The autoimmune reactions result in the development of small intestinal mucosal villous atrophy with crypt hyperplasia and mucosal inflammation. Symptoms of celiac disease can vary from individual to individual, and may include one or more of fatigue, chronic diarrhea, constipation, malabsorption of nutrients, weight loss, abdominal distension, anemia, as well as a substantially enhanced risk for the development of osteoporosis and intestinal malignancies (lymphoma and carcinoma).

Treatment for gluten intolerance commonly involves a lifelong strict gluten-free diet. However, gluten-free diet is inconvenient, restrictive, and gluten is difficult to avoid. Therefore, effective alternative treatments of gluten intolerance are needed.

A number of bacterial species are known to cause gastrointestinal tract infection. Although current treatment for such infections relies heavily on antibiotics, an increasing number of bacterial infections are found to be resistant to at least some antibiotics. In addition, some bacteria species form endospores that make them especially difficult to eradicate. Gastric proteases such as pepsin are generally unable to kill endospores, for example because of the inability to break down the proteinaceous coat that protects the endospore. Therefore, effective alternative treatments of bacterial infection are needed.

SUMMARY OF THE INVENTION

This invention relates to the discovery that the enzyme nepenthesin possesses a high proteolytic activity for cleaving proteins and oligopeptides (including gluten), especially at low pH (e.g., about 2 to 3). Nepenthesin (EC 3.4.23.12) is an aspartic protease of plant origin that can be isolated or concentrated from a variety of plant sources, such as the pitcher secretions of Nepenthes, a carnivorous pitcher plant, commonly known as monkey cups in tropical regions. Tökés et al., Digestive Enzymes Secreted by the Carnivorous Plant Nepenthes macferlanei L., Planta (Berl.) 119, 39-46 (1974). It has been found that the activity of nepenthesin is about 1000 fold higher than that of that of pepsin (EC 3.4.23.1), an enzyme present in the stomach of humans partly responsible for degrading food proteins into peptides. It has also been found that nepenthesin has a much more relaxed specificity than pepsin, efficiently cleaving after most amino acid residues with the exception of amino acid residues G, S, T, V, I and W. Notably, it cleaves after amino acid residues K, R and P. By comparison, pepsin presents high-efficiency cleavage for the hydrophobic amino acid residues F, L and M but cleavage after amino acid residues P, H, K and R is essentially forbidden.

Nepenthesin has two known isoforms: nepenthesin I (known to have two variants: nepenthesin Ia and nepenthesin Ib) and II. Both isoforms are found have a higher cleavage affinity for both amino acids P and Q than pepsin. Surprisingly, it has been discovered that the combination of nepenthesin I and nepenthesin II has a slightly different cleavage affinity than nepenthesin I alone. Specifically, extract comprising nepenthesin I and nepenthesin II cleaves more efficiently after the amino acid Q on the N-terminal side of gliadin and the amino acid P on the C-terminal side of gliadin than does nepenthesin I alone.

Gluten intolerance and associated conditions and symptoms, such as celiac disease and/or dermatitis herpetiformis, are caused by the patient's abnormal immune response to gluten in the small intestinal mucosa. Certain gluten components are resistant to cleavage by gastric and pancreatic peptidases such as pepsin, trypsin, chymotrypsin, and the like. While not wishing to be bound by any theories, it is contemplated that degradation of gluten to non-toxic peptides by nepenthesin prior to arriving at the intestinal tract of a patient decreases the levels of toxic gluten proteins or peptides going into the small intestine. As nepenthesin is acid stable, it is compatible with the stomach pH and digests gluten so as to modulate a patient's gluten intolerance or related conditions or symptoms.

Given its high activity at low pH and its broad spectrum of activity, nepenthesin is especially useful in digesting gluten proteins in the stomach. The degradation of gluten to non-toxic peptides is also referred to as detoxification of gluten. While not wishing to be bound by any theories, it is contemplated that degradation of gluten, which is comprised of proline- and glutamine-rich proteins, to non-toxic peptides can be more efficiently achieved by nepenthesin than by stomach enzymes such as pepsin.

This invention further relates to the use of nepenthesin, such as nepenthesin I and/or nepenthesin II and derivatives thereof in treating bacterial infections of the gastrointestinal tract. Given its high activity at low pH and its broad spectrum of activity, nepenthesin is useful in treating bacterial infections of the gastrointestinal tract. Without being bound by theory, it is believed that nepenthesin is more efficient than stomach enzymes at disrupting bacterial cell walls and endospore coats.

In one aspect, provided are methods for modulating gluten intolerance in a patient with gluten intolerance, which method comprises administering an effective amount of nepenthesin, such as nepenthesin I and/or nepenthesin II or a derivative thereof to said patient. In one aspect, nepenthesin I or a derivative thereof is administered to said patient. In one aspect, nepenthesin II or a derivative thereof is administered to said patient. In one aspect, a mixture of nepenthesin I and nepenthesin II or derivatives thereof is administered to said patient.

In one embodiment, nepenthesin, such as nepenthesin I and/or nepenthesin II or a derivative thereof is administered as a food additive such that nepenthesin or the derivative thereof is combined with gluten containing food to modulate or inhibit conditions associated with gluten intolerance. Nepenthesin or a derivative thereof can be used alone or in combination with such food. In one aspect, nepenthesin I or a derivative thereof is used. In one aspect, nepenthesin II or a derivative thereof is used. In one aspect, a mixture of nepenthesin I and nepenthesin II or derivatives thereof is used.

In another aspect, provided are methods for modulating a condition mediated by gluten intolerance in a patient which method comprises administering an effective amount of nepenthesin, such as nepenthesin I and/or nepenthesin II or a derivative thereof to said patient. Such conditions include, by way of example only, celiac disease, wheat allergy, gluten sensitivity and/or dermatitis herpetiformis. In one aspect, nepenthesin I or a derivative thereof is administered to said patient. In one aspect, nepenthesin II or a derivative thereof is administered to said patient. In one aspect, a mixture of nepenthesin I and nepenthesin II or derivatives thereof is administered to said patient.

In any event, nepenthesin, such as nepenthesin I and/or nepenthesin II or a derivative thereof can be administered to the patient prior to, concurrently with, or shortly after consumption of a food comprising gluten or suspected of comprising gluten. In one aspect, nepenthesin I or a derivative thereof is administered to said patient. In one aspect, nepenthesin II or a derivative thereof is administered to said patient. In one aspect, a mixture of nepenthesin I and nepenthesin II or derivatives thereof is administered to said patient.

In another aspect, provided are methods for modulating gluten intolerance or an associated condition, such as celiac disease, wheat allergy, gluten sensitivity or dermatitis herpetiformis, in a patient in need thereof, comprising treating a food comprising gluten or suspected of comprising gluten with an effective amount of nepenthesin prior to consumption by the patient. In one aspect, said food is treated with an effective amount of nepenthesin I or a derivative thereof. In one aspect, said food is treated with an effective amount of nepenthesin II or a derivative thereof. In one aspect, said food is treated with an effective amount of a mixture of nepenthesin I and nepenthesin II or derivatives thereof.

In another aspect, provided are foods or compositions comprising nepenthesin, such as nepenthesin I and/or nepenthesin II or a derivative thereof. In one aspect, said food or composition comprises nepenthesin I or a derivative thereof. In one aspect, said food or composition comprises nepenthesin II or a derivative thereof. In one aspect, said food or composition comprises a mixture of nepenthesin I and nepenthesin II or derivatives thereof.

In another aspect, provided is a composition for optimizing cleavage of a gluten protein at a proline residue, comprising a mixture of recombinant nepenthesin I and recombinant nepenthesin II. In one aspect, provided is a composition for optimizing cleavage of a gluten protein at a glutamine residue, comprising a mixture of recombinant nepenthesin I and recombinant nepenthesin II.

In another aspect, provided is a composition comprising fragmented gluten, wherein the composition is enriched in gluten fragments produced by cleavage of the gluten at a proline residue of the gluten. In one aspect, provided is a composition comprising fragmented gluten, wherein the composition is enriched in gluten fragments produced by cleavage of the gluten at a glutamine residue.

In another aspect, provided is a method for digesting proteins comprising gluten which method comprises contacting said proteins with an effective amount of nepenthesin I and/or nepenthesin II.

In another aspect, provided is a method for producing recombinant nepenthesin, such as nepenthesin I and/or nepenthesin II or a derivative thereof, the method comprising expressing in a chosen host organism a nucleic acid sequence which encodes said nepenthesin or homologue thereof and which nucleic acid sequence has been inserted into an appropriately designed vector; in order to obtain said nepenthesin or a homologue thereof. In one aspect, the recombinant nepenthesin is nepenthesin I or a derivative thereof. In one aspect, the recombinant nepenthesin is nepenthesin II or a derivative thereof. In one aspect, the recombinant nepenthesin is a mixture of nepenthesin I and nepenthesin II or derivatives thereof.

In another aspect, provided is a composition comprising recombinant nepenthesin or a derivative thereof. In one aspect, the recombinant nepenthesin is recombinant nepenthesin I or a derivative thereof. In one aspect, the recombinant nepenthesin is recombinant nepenthesin II or a derivative thereof. In one aspect, the recombinant nepenthesin is a mixture of recombinant nepenthesin I and recombinant nepenthesin II or derivatives thereof.

In another aspect, provided are methods for preventing or treating bacterial or parasitic infections of the gastrointestinal tract in a patient, which method comprises administering a therapeutically effective amount of nepenthesin, such as nepenthesin I and/or nepenthesin II or a derivative thereof to said patient. In one aspect, nepenthesin I or a derivative thereof is administered to said patient. In one aspect, nepenthesin II or a derivative thereof is administered to said patient. In one aspect, a mixture of nepenthesin I and nepenthesin II or derivatives thereof is administered to said patient.

These and other aspects of the invention will be further described in the text that follows.

BRIEF DESCRIPTION OF THE DRAWINGS

FIG. 1 shows nepenthesin cleavage preferences at (A) the P1 or N-terminal side of the cleavage site and at (B) the P1' or C-terminal side of the cleavage site. Data is grouped according to amino acid type and compared to a similar rendering of pepsin data from Hamuro et al. Specificity of immobilized porcine pepsin in H/D exchange compatible conditions. *Rapid Communications in Mass Spectrometry*

22(7):1041-1046 (2008). Hatched bars indicate nepenthesin digestion and the white bars pepsin digestion. The % cleavage represents the number of observed cleavages at the given residue, relative to the total number of the given residues in the set. Nepenthesin data were obtained from digests of six denatured proteins, as described in Example 2.

FIG. 2 (FIGS. 2A-2D) shows an XRCC4 (SEQ ID NO:2) composite peptide sequence map, arranged according to domain type. The peptides were obtained using pepsin digestion at four different enzyme:substrate ratios (65:1 to 520:1, white/top set of bars), and using nepenthesin digestion at four different enzyme:substrate ratios (0.0075:1 to 0.38:1, spotted/bottom set of bars). FIGS. 2A and 2B represent the head region of XRCC4, and FIGS. 2C and 2D represent the tail and stalk regions of XRCC4.

Figure 3:
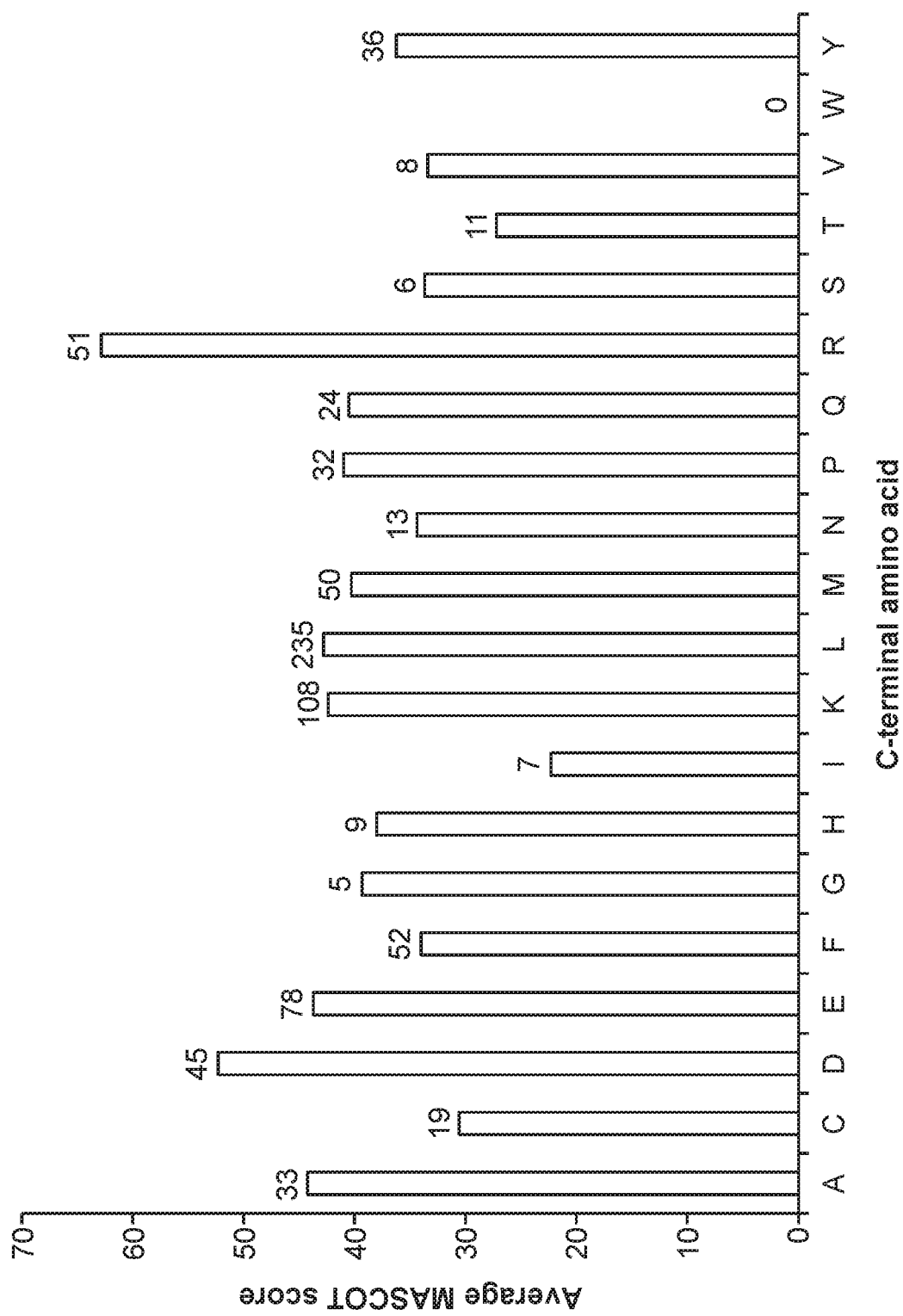

FIG. 3 shows the average MASCOT score of peptides obtained after nepenthesin digestion, grouped by C-terminal amino acid. The number of peptides used for each calculation is associated with the terminal amino acid, above the bar. Peptides were obtained from the digests of six denatured proteins, as described in Example 2.

FIG. 4 shows peptide ion chromatograms (PICs) of XRCC4 digested with (A) nepenthesin and (B) pepsin over a range of enzyme:substrate ratios (shown in the legend). PICs for enzymatic digestion were generated from the same mass-load of substrate on column.

Figure 5:
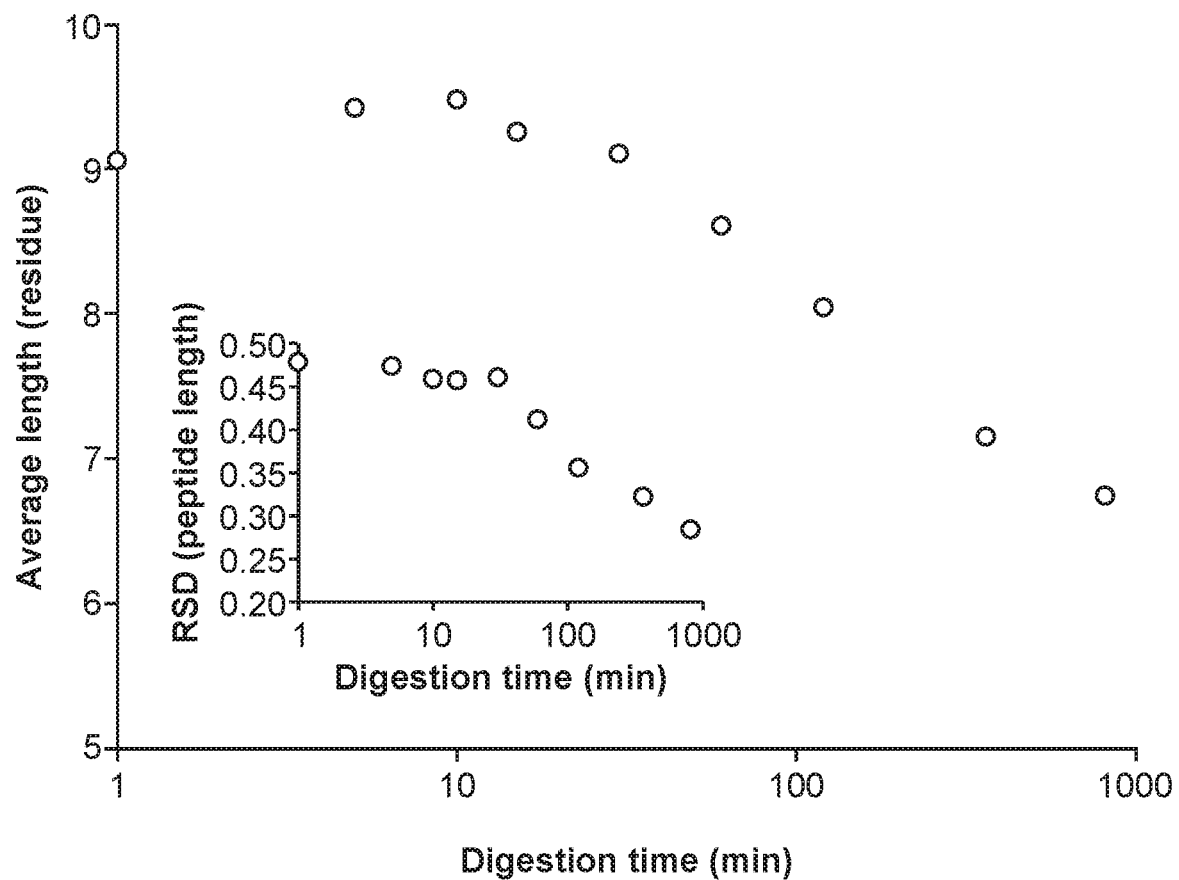

FIG. 5 shows the average length of all peptides identified from a nepenthesin digestion of gliadin from wheat, using LC-MS/MS, after 1, 5, 10, 15, 30, 60, 130, 360 or 810 minutes at 37° C. A 95% confidence cut-off (p<0.05) on the scores were used to remove false positive identification. Relative standard deviation of the peptide length is shown in the inset figure.

Figure 6:
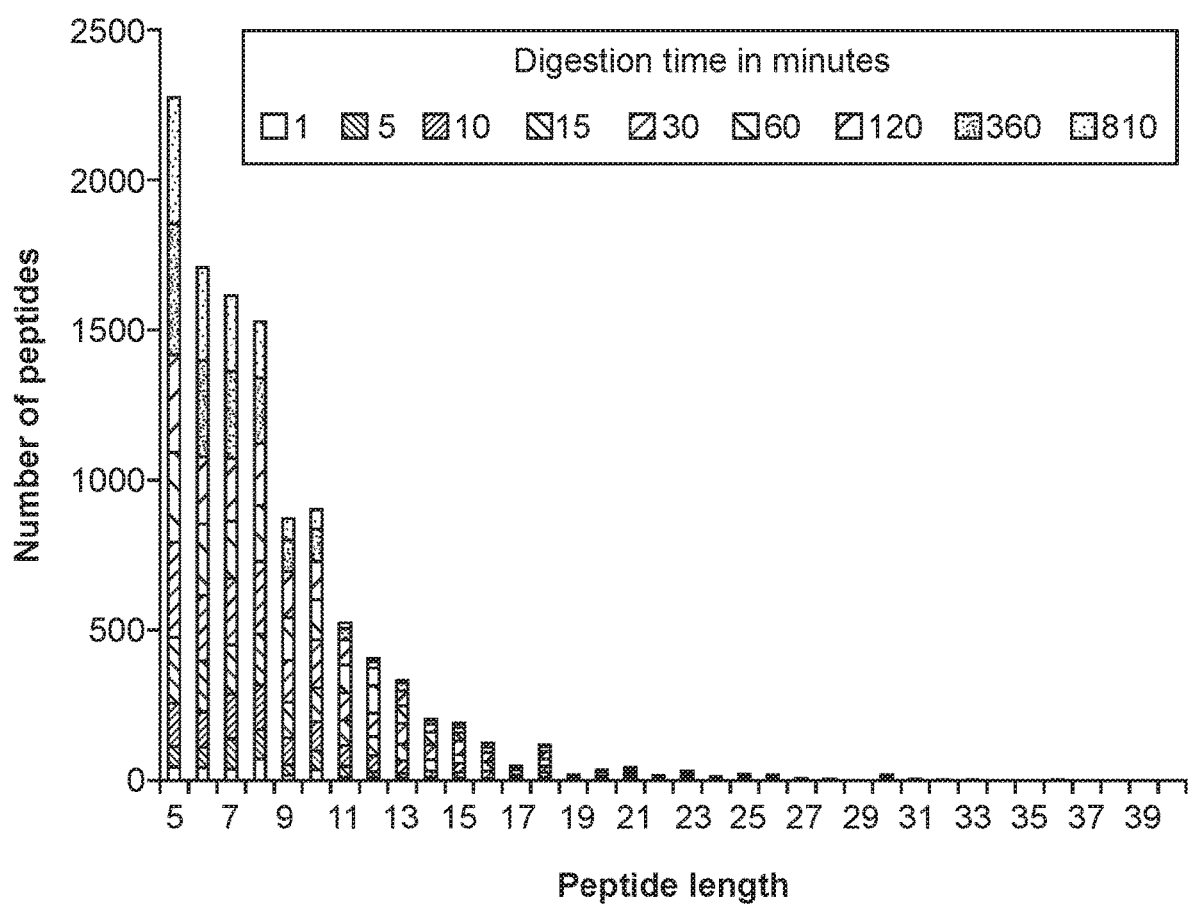

FIG. 6 displays the number of peptides identified by LC-MS/MS after 1, 5, 10, 15, 30, 60, 130, 360 or 810 minutes digestion at 37° C., grouped by length. Data as in FIG. 5.

Figure 7:
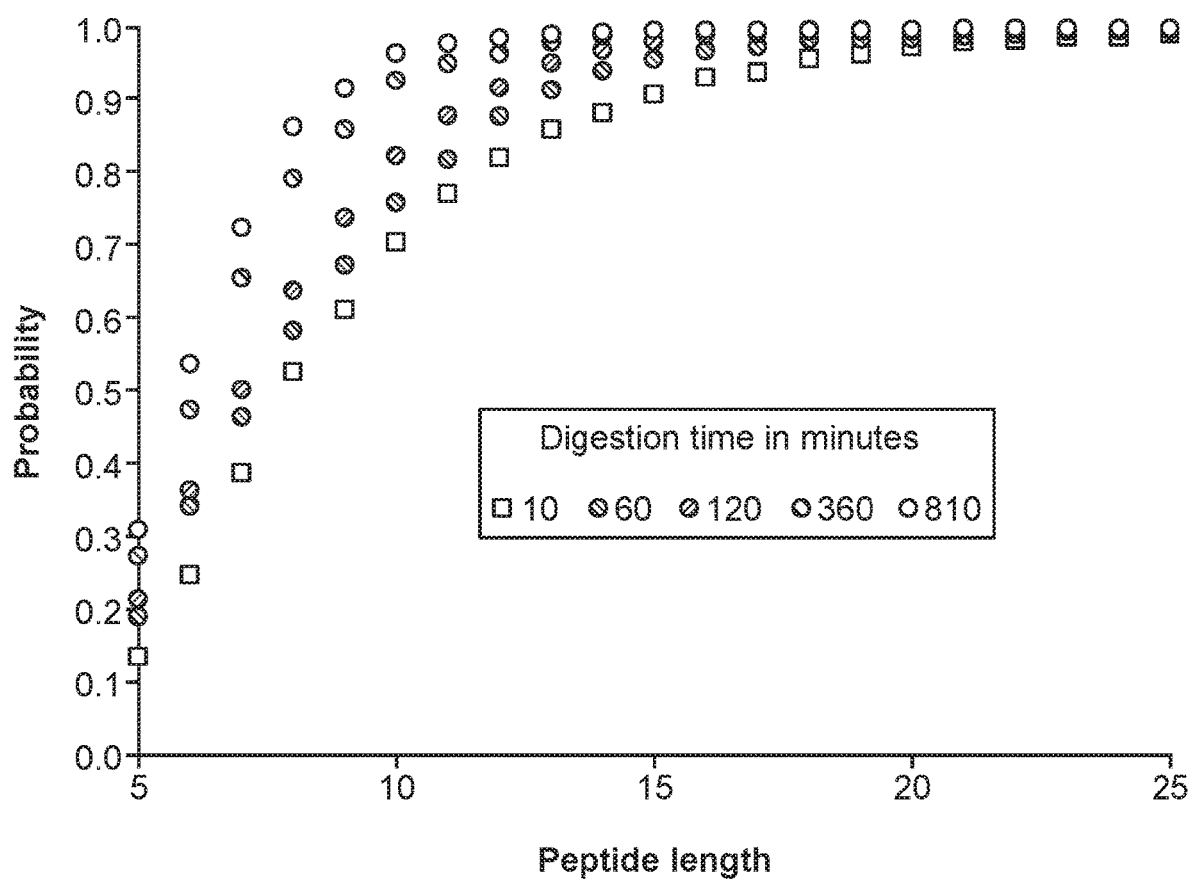

FIG. 7 displays the same data as in FIG. 5, as a probability of obtaining a certain length after 10, 60, 120, 360 or 810 minutes digestion at 37° C.

FIG. 8 shows nepenthesin cleavage preferences at (A) the P1 or N-terminal side of the cleavage site and at (B) the P1' or C-terminal side of the cleavage site. Left bars for each reside indicate digestion with nepenthesin extract, the middle bars indicate digestion with purified nepenthesin extract, and the right bars with recombinant nepenthesin I. The % cleavage represents the number of observed cleavages at the given residue, relative to the total number of peptides present. Nepenthesin data were obtained from digests of gliadin, as described in Example 9.

FIG. 9 shows an alignment of the protein sequences for nepenthesin I from *Nepenthes mirabilis* (SEQ ID NO: 3), *Nepenthes gracilis* (SEQ ID NO: 5), *Nepenthes alata* (SEQ ID NO: 4), *Zea mays* (SEQ ID NO: 8), and *Oryza sativa* (SEQ ID NO: 9), and nepenthesin II from *Nepenthes mirabilis* (SEQ ID NO: 6), *Nepenthes gracilis* (SEQ ID NO: 7), *Zea mays* (SEQ ID NO: 11), and *Oryza sativa* (SEQ ID NO: 10).

Figure 10:
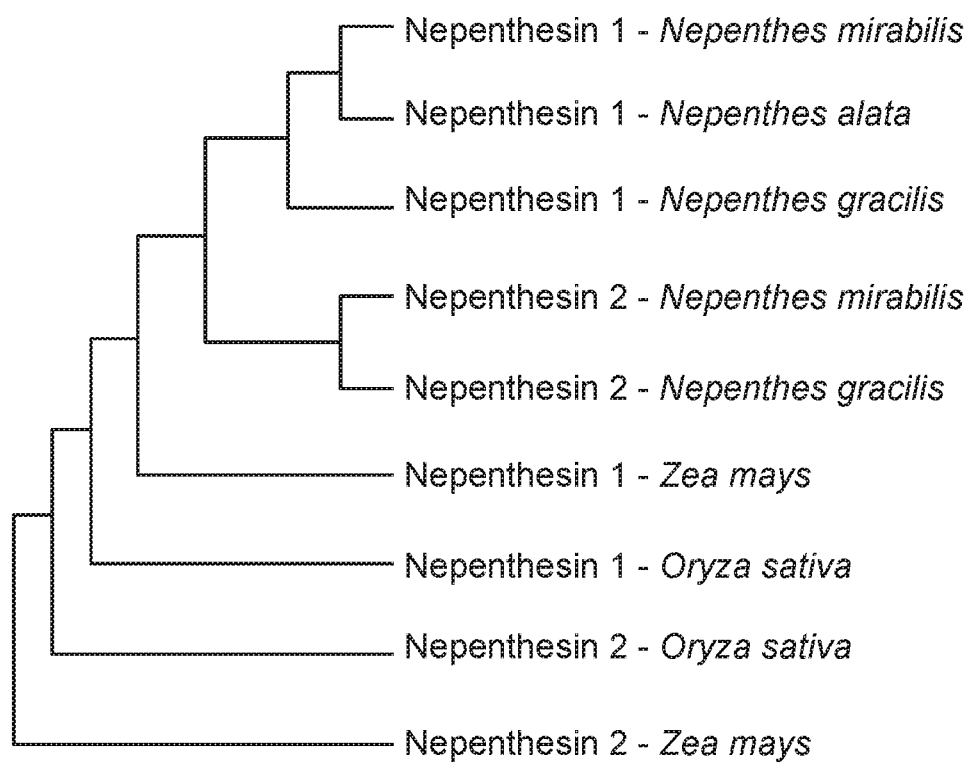

FIG. 10 shows a phylogenetic tree indicating the relatedness of nepenthesin proteins between different species.

DETAILED DESCRIPTION OF THE INVENTION

I. Definitions

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present disclosure employs, unless otherwise indicated, conventional techniques of molecular biology (including recombinant techniques), microbiology, cell biology, biochemistry and immunology, which are within the skill of the art. Such techniques are explained fully in the literature for example in the following publications. See, e.g., Sambrook and Russell eds. MOLECULAR CLONING: A LABORATORY MANUAL, 3$^{rd}$ edition (2001); the series CURRENT PROTOCOLS IN MOLECULAR BIOLOGY (F. M. Ausubel et al. eds. (2007)); the series METHODS IN ENZYMOLOGY (Academic Press, Inc., N.Y.); PCR 1: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1999)); CULTURE OF ANIMAL CELLS: A MANUAL OF BASIC TECHNIQUE (R. I. Freshney 5$^{th}$ edition (2005)); OLIGONUCLEOTIDE SYNTHESIS (M. J. Gait ed. (1984)); Mullis et al. U.S. Pat. No. 4,683,195; NUCLEIC ACID HYBRIDIZATION (B. D. Hames & S. J. Higgins eds. (1984)); NUCLEIC ACID HYBRIDIZATION (M. L. M. Anderson (1999)); TRANSCRIPTION AND TRANSLATION (B. D. Hames & S. J. Higgins eds. (1984)); IMMOBILIZED CELLS AND ENZYMES (IRL Press (1986)); B. Perbal, A PRACTICAL GUIDE TO MOLECULAR CLONING (1984); GENE TRANSFER VECTORS FOR MAMMALIAN CELLS (J. H. Miller and M. P. Calos eds. (1987) Cold Spring Harbor Laboratory); GENE TRANSFER AND EXPRESSION IN MAMMALIAN CELLS (S. C. Makrides ed. (2003)) IMMUNOCHEMICAL METHODS IN CELL AND MOLECULAR BIOLOGY (Mayer and Walker, eds., Academic Press, London (1987)); WEIR'S HANDBOOK OF EXPERIMENTAL IMMUNOLOGY (L. A. Herzenberg et al. eds (1996)).

As used in the specification and claims, the singular form "a", "an" and "the" include plural references unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

As used herein, the term "gluten" generally refers to the proteins present in wheat or related grain species, including barley and rye, which have potential harmful effect to certain individuals. Gluten proteins include gliadins such as α-gliadins, β-gliadins, γ-gliadins and ω-gliadins, which are monomeric proteins, and glutenins which are highly heterogeneous mixture of aggregates of high molecular weight and low-molecular-weight subunits held together by disulphide bonds. Many wheat gluten proteins have been characterized, see, for example, Woychik et al., Amino Acid Composition of Proteins in Wheat Gluten, *J. Agric. Food Chem.*, 9(4), 307-310 (1961). The term gluten as used herein also includes oligopeptides that can be derived from normal human digestion of gluten proteins from gluten containing foods and cause the abnormal immune response. Some of these oligopeptides are resistant to normal digestive enzymes. Gluten, including the above-mentioned proteins and oligopeptides, is believed to act as antigens for T cells in celiac sprue in patients with gluten intolerance.

The term "nepenthesin" refers to the aspartic protease having the Enzyme Commission number EC 3.4.23.12, and includes all isoforms and variants of nepenthesin such as nepenthesin I and nepenthesin II, and recombinant nepenthesin, and salts thereof. Salts refer to those salts formed by nepenthesin with one or more base or one or more acid which retain the biological effectiveness and properties of the free nepenthesin, and which are not biologically or otherwise undesirable. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Acids that can form salts include, but are not limited to, inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

Nepenthesin derivatives include biological equivalents, fragments and extended nepenthesin, and salts thereof, that retain proteolytic activity. In some embodiments, nepenthesin derivatives include biological equivalents of nepenthesin. "Biological equivalents" include those having at least about 80% homology or identity or alternatively, at least about 85%, or alternatively at least about 90%, or alternatively at least about 95%, or alternatively 98% homology with nepenthesin, or alternatively a polypeptide or protein encoded by a polynucleotide that hybridizes under stringent conditions to the nucleotide sequence encoding nepenthesin or its complement, while maintaining the desired structure and exhibiting at least part of the proteolytic activity of nepenthesin.

In some embodiments, the nepenthesin derivative is a fragment of nepenthesin having at least about 20 contiguous amino acids of the full nepenthesin protein, or at least about 50 contiguous amino acids, or comprising 100 or more contiguous amino acids, up to the complete protein of nepenthesin. Nepenthesin derivatives also include nepenthesin having additional sequences.

In some embodiments, a nepenthesin derivative has at least about 10% of the proteolytic activity of nepenthesin, or at least about 50%, or at least about 70%, or at least about 90% of the proteolytic activity of nepenthesin or 100% or more of the proteolytic activity of nepenthesin.

As used herein, the term "biological equivalent thereof" is intended to be synonymous with "equivalent thereof" which when referring to a reference protein, antibody, polypeptide or nucleic acid, intends those having minimal homology while still maintaining desired structure or functionality. In an alternative embodiment, the term "biological equivalent of" a polynucleotide refers to one that hybridizes under stringent conditions to the reference polynucleotide or its complement. Unless specifically recited herein, it is contemplated that any polynucleotide, polypeptide or protein mentioned herein also includes equivalents thereof. For example, an equivalent intends at least about 80% homology or identity and alternatively, at least about 85%, or alternatively at least about 90%, or alternatively at least about 95%, or alternatively 98% percent, or alternatively 99% percent homology or sequence identity and exhibits substantially equivalent biological activity to the reference protein, polypeptide or nucleic acid.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. One alignment program is BLAST, using default parameters. Examples of the programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

Suitable expression vectors include vectors capable of expressing a polynucleotide operatively linked to a regulatory element, such as a promoter region and/or an enhancer that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors include those that are replicable in eukaryotic cells and/or prokaryotic cells and those that remain episomal or those which integrate into the host cell genome.

As used herein, the term "vector" refers to a non-chromosomal nucleic acid comprising an intact replicon such that the vector may be replicated when placed within a cell, for example by a process of transformation. Vectors may be viral or non-viral. Viral vectors include retroviruses, adenoviruses, herpesvirus, papovirus, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA.

Non-viral vector may include plasmid that comprises a heterologous polynucleotide capable of being delivered to a target cell, either in vitro, in vivo or ex-vivo. The heterologous polynucleotide can comprise a sequence of interest and can be operably linked to one or more regulatory elements and may control the transcription of the nucleic acid sequence of interest. As used herein, a vector need not be capable of replication in the ultimate target cell or subject. The term vector may include expression vector and cloning vector.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

"Hybridization" refers to hybridization reactions that can be performed under conditions of different "stringency". Conditions that increase the stringency of a hybridization reaction are widely known and published in the art: see, for example, Sambrook and Russell eds. (2001) Molecular Cloning: A Laboratory Manual, 3rd edition. Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours and washes of increasing duration, increasing frequency, or decreasing buffer concentrations.

In one embodiment, "therapeutically effective amount" refers to that amount of a compound that results in prevention or amelioration of symptoms in a patient or a desired biological outcome, e.g., improved clinical signs, delayed onset of disease, etc. The effective amount can be determined by one of ordinary skill in the art. The selected dosage level can depend upon the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved.

"Concurrent administration," or co-treatment, as used herein includes administration of the agents together, or before or after each other.

The term "modulate" or "modulating" means any treatment of a disease or disorder in a subject, such as a mammal, including:
  preventing or protecting against the disease or disorder, that is, causing the abnormal biological reaction or symptoms not to develop;
  inhibiting the disease or disorder, that is, arresting or suppressing the development of abnormal biological reactions and/or clinical symptoms; and/or
  relieving the disease or disorder that is, causing the regression of abnormal biological reactions and/or clinical symptoms.

As used herein, the term "preventing" refers to the prophylactic treatment of a patient in need thereof. The prophylactic treatment can be accomplished by providing an appropriate dose of a therapeutic agent to a subject at risk of suffering from an ailment, thereby substantially averting onset of the ailment.

As used herein, the term "condition" refers to a disease state for which the compounds, compositions and methods provided herein are being used.

As used herein, the term "patient" or "subject" refers to mammals and includes humans and non-human mammals. In particular embodiments herein, the patient or subject is a human.

The term "about" when used before a numerical value indicates that the value may vary within a reasonable range, such as ±5%, ±1%, and ±0.2%.

II. Methods

In one aspect, provided are methods for modulating gluten intolerance in a patient with gluten intolerance which method comprises administering an effective amount of nepenthesin, such as nepenthesin I and/or nepenthesin II, or a derivative thereof to said patient.

In one embodiment, nepenthesin or a derivative thereof is administered as a food additive such that nepenthesin or a derivative thereof is combined with gluten containing food to modulate or inhibit conditions associated with gluten intolerance. Nepenthesin or a derivative thereof can be used alone or in combination with such food.

In another aspect, provided are methods for modulating a condition mediated by gluten intolerance in a patient which method comprises administering an effective amount of nepenthesin or a derivative thereof to said patient. Such conditions include by way of example only celiac disease, wheat allergy, gluten sensitivity and dermatitis herpetiformis. Nepenthesin or a derivative thereof can be administered to the patient prior to, concurrently with, or shortly after ingestion of a food comprising gluten or suspected of comprising gluten.

In some embodiments, nepenthesin such as nepenthesin I and/or nepenthesin II or a derivative thereof is administered to the patient prior to ingestion by the patient of the food comprising gluten or suspect of comprising gluten. In some embodiments, nepenthesin or a derivative thereof is administered within a period that nepenthesin or the derivative thereof is at least partially effective (for example, at least about 10%, 20%, 50%, 70%, 90% of original activity) in degrading gluten in the food that the patient will ingest. In some embodiments, nepenthesin or a derivative thereof is administered not more than about 4 hours, 3 hours, 2 hours, 1 hour, or 30 minutes prior to ingestion of the food by the patient.

In some embodiments, nepenthesin or a derivative thereof is administered to the patient concurrently with ingestion by the patient of the food comprising gluten or suspect of comprising gluten. In some embodiments, nepenthesin or a derivative thereof is administered with the food, such as an ingredient or additive to the food. In some embodiments, nepenthesin or a derivative thereof is administered separately from the food.

In some embodiments, nepenthesin or a derivative thereof is administered to the patient shortly after ingestion by the patient of the food comprising gluten or suspect of comprising gluten. In some embodiments, nepenthesin or a derivative thereof is administered within a period that at least part (for example, at least about 10%, 20%, 50%, 70%, 90%) of the gluten in the food is still in the stomach of the patient. In some embodiments, nepenthesin or a derivative thereof is administered not more than 4 hours, 3 hours, 2 hours, 1 hour, or 30 minutes after ingestion of the food by the patient.

In another aspect, provided are methods for preventing or treating bacterial or parasitic infections of the gastrointestinal tract in a patient, which method comprises administering a composition comprising an effective amount of nepenthesin or a derivative thereof to said patient. By way of example only, such bacterial infections may be caused by bacteria such as *Bacillus cereus, Bacillus anthracis, Helicobacter pylori, Salmonella, Campylobacter, E. coli, Shigella, Clostridium difficile, Vibrio cholerae, Staphylococcus aureus, Clostridium perfringens, Clostridium botulinum, Campylobacter jejuni*, and *Listeria monocytogenes*. In one aspect, said composition comprises nepenthesin I or a derivative thereof. In one aspect, said composition comprises nepenthesin II or a derivative thereof. In one aspect, said composition comprises a mixture of nepenthesin I and nepenthesin II or derivatives thereof.

*C. difficile* are naturally-occurring intestinal flora in a small subset of the population. However, most people are exposed to *C. difficile* as patients in a hospital, nursing home, or similar facility by ingesting spores of the bacteria. *C. difficile* can overrun the gastrointestinal tract under opportunistic conditions, usually due to treatment with a broad-spectrum antibiotic which destroys the normal gut flora. The bacteria release toxins that can cause bloating, diarrhea, and severe abdominal pain. *C. difficile* infections are the most common cause of pseudomembranous colitis, which in rare cases progress to life-threatening toxic megacolon. The rate of *C. difficile* is acquired by a significant number of patients with long hospital stays: acquisition is estimated to be 13% in patients with hospital stays of up to two weeks, and 50% in those with hospital stays longer than four weeks. Clabots, C R; Johnson, S; Olson, M M; Peterson, L R; Gerding, D N (September 1992). "Acquisition of *Clostridium difficile* by hospitalized patients: evidence for colonized new admissions as a source of infection". *Journal of Infectious Diseases* 166 (3): 561-7.

*Helicobacter* have been found living in the lining of the upper gastrointestinal tract, as well as the liver of mammals and some birds. *H. pylori* infects up to 50% of the human population and may be pathogenic to humans. *H. pylori* is strongly associated with peptic ulcers, chronic gastritis, duodenitis, and stomach cancer. Other *Helicobacter* species have also been associated with these conditions, including *H. suis, H. felis, H. bizzozeronii* and *H. salomonis*.

In one aspect, a therapeutically effective amount of the pharmaceutical composition of the invention is administered to a patient known to have or suspected of having an infection of the gastrointestinal tract. In another aspect, the composition is administered to a patient at risk of being infected, for example a patient with a long hospital stay and/or a patient who is prescribed a broad spectrum antibiotic.

Typically, nepenthesin such as nepenthesin I and/or nepenthesin II or a derivative thereof is administered in an amount that is safe and sufficient to produce the desired effect of gluten detoxification or treating bacterial infection. The dosage of the compounds of nepenthesin or derivatives thereof can vary depending on many factors such as the particular nepenthesin or derivative thereof administered, the patient's sensitivity to gluten, the amount and types of gluten containing food ingested, the pharmacodynamic properties, the mode of administration, the age, health and weight of the recipient, the nature and extent of the symptoms, the frequency of the treatment and the type of concurrent treatment, if any, and the clearance rate of the compound. One of skill in the art can determine the appropriate dosage based on the above factors. The compounds may be administered initially in a suitable dosage that may be adjusted as required, depending on the clinical response. The amount of nepenthesin such as nepenthesin I and/or nepenthesin II or a derivative thereof which will be effective in the treatment of a disease correlated with or caused by infection with pathogenic bacteria, for example, can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances.

The dosage or dosing regime of an adult patient may be proportionally adjusted for children and infants, and also adjusted for other administration or other formats, in proportion for example to molecular weight or immune response. Administration or treatments may be repeated at appropriate intervals, at the discretion of the physician.

Generally, nepenthesin or a derivative thereof is administered when needed, such as when the patient will be or is consuming or has consumed a food comprising gluten or suspected of comprising gluten, or having or suspected of having a bacterial infection. Alternatively, a pharmaceutical composition comprising nepenthesin or a derivative thereof may be administered to a patient in need thereof. In any case, it can be administered in dosages of about 0.001 mg to about 1000 mg/kg body weight per day, or about 1 mg to about 100 g per dose for an average person. In some embodiments, nepenthesin or a derivative thereof can be administered at 0.001, 0.01, 0.1, 1, 5, 10, 50, 100, 500, or 1000 mg/kg body weight per day, and ranges between any two of these values (including endpoints). In some embodiments, nepenthesin or a derivative thereof can be administered at 1 mg, 10 mg, 100 mg, 200 mg, 500 mg, 700 mg, 1 g, 10 g, 20 g, 50 g, 70 g, 100 g per dose, and ranges between any two of these values (including endpoints). In some embodiments, it may be administered once, twice, three times, etc. a day, depending on the number of times the patient ingests a gluten containing food, or depending on the type, severity, or risk of bacterial or parasitic infection.

The compounds of this invention can be administered as the sole active agent or they can be administered in combination with other agents (simultaneously, sequentially or separately, or through co-formulation), including other compounds that demonstrate the same or a similar therapeutic activity and that are determined to safe and efficacious for such combined. administration.

In some embodiments, nepenthesin or a derivative thereof is administered with another enzyme, such as a gastric protease (e.g., pepsin and pepsinogen), another aspartic protease, such as those described by Chen et al., Aspartic proteases gene family in rice: Gene structure and expression, predicted protein features and phylogenetic relation, *Gene* 442:108-118 (2009), and enzymes such as prolyl endopeptidase (PEP), dipeptidyl peptidase IV (DPP IV), and dipeptidyl carboxypeptidase (DCP) or cysteine proteinase B described in U.S. Pat. No. 7,910,541.

In some embodiments, nepenthesin is administered to the patient with another agent. Non-limiting examples of agents that can be administered with nepenthesin include inhibitors of tissue transglutaminase, anti-inflammatory agents such as HMG-CoA reductase inhibitors (e.g., compactin, lovastatin, simvastatin, pravastatin and atorvastatin), leukotriene receptor antagonists (e.g., montelukast and zafirlukast), COX-2 inhibitors (e.g., celecoxib and rofecoxib), p38 MAP kinase inhibitors (e.g., BIRB-796); mast cell-stabilizing agents such as sodium chromoglycate (chromolyn), pemirolast, proxicromil, repirinast, doxantrazole, amlexanox nedocromil and probicromil, anti-ulcer agents, anti-allergy agents such as anti-histamine agents (e.g., acrivastine, cetirizine, desloratadine, ebastine, fexofenadine, levocetirizine, loratadine and mizolastine), inhibitors of transglutaminase 2 (TG2), anti-TNFα agents, and antibiotics.

In some embodiments, nepenthesin is co-administered with an antibiotic, such as a penicillin, a cephalosporin, a carbapenem, a polymixin, a rifamycin, a lipiarmycin, a quinolone, a sulfonamide, a β-lactam, a fluoroquinolone, a glycopeptide, a ketolide, a lincosamide, a streptogramin, an aminoglycoside, a macrolide, a tetracycline, a cyclic lipopeptide, a glycylcycline, or an oxazolidinone. Antibiotics in these classes are known in the art.

In some embodiments, nepenthesin is co-administered with an anti-infective agent (for example, an antifungal triazole or amphotericin). These may include carbapenems, for example meropenem or imipenem, to broaden the therapeutic effectiveness.

Also provided herein is the use of nepenthesin or a derivative thereof in the manufacture of a medicament for the treatment or prevention of one of the aforementioned conditions and diseases Compositions Nepenthesin such as nepenthesin I and/or nepenthesin II or a derivative thereof can be administered in a variety of compositions alone or with appropriate, pharmaceutically acceptable carriers or diluents or dietary ingredients.

Accordingly, in another aspect, provided herein is a composition comprising nepenthesin or a derivative thereof. In some embodiments, the composition is an edible composition. In some embodiments, the composition is a dietary supplement. In some embodiments, the composition is a pharmaceutical composition. In some embodiments, the composition is a food or food additive. The compositions may be formulated into solid, semi-solid, or liquid forms, such as tablets, capsules, powders, granules, ointments, solutions, injections, gels, and microspheres. Administration of nepenthesin or a derivative thereof can be achieved in various ways, for example, by oral administration.

In some embodiments, the pharmaceutical compositions comprise a therapeutically effective amount of an agent and a pharmaceutically acceptable carrier. In a particular embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, incorporated in its entirety by reference herein. Such compositions will contain a therapeutically effective amount of nepenthesin or derivative thereof, preferably in purified form, together with a suitable amount of carrier so as to provide the form for proper administration to the subject. The formulation should suit the mode of administration.

For oral administration, nepenthesin or a derivative thereof can be used alone or in combination with appropriate additives to make tablets, powders, granules, capsules, syrups, liquids, suspensions, etc. For example, solid oral forms of nepenthesin or a derivative thereof can be prepared with conventional additives, disintegrators, lubricants, diluents, buffering agents, moistening agents, preservatives and flavoring agents. Non-limiting examples of excipients include lactose, mannitol, corn starch, potato starch, crystalline cellulose, cellulose derivatives, acacia, corn starch, sodium carboxymethylcellulose, talc, magnesium stearate, flavors and colors. In some embodiments, the formulation releases nepenthesin or a derivative thereof in the stomach of the patient so that gluten can be degraded by the nepenthesin or derivative thereof.

Nepenthesin or a derivative thereof can be lyophilized from an aqueous solution optionally in the presence of appropriate buffers (e.g. phosphate, citrate, histidine, imidazole buffers) and excipients (e.g. cryoprotectants such as sucrose, lactose, trehalose). Lyophilized cakes can optionally be blended with excipients and made into different forms.

In another aspect, provided are methods for treating gluten intolerance or an associated condition, such as celiac disease, wheat allergy, gluten sensitivity and dermatitis herpetiformis, in a patient in need thereof, comprising treating a food comprising gluten or suspected of comprising gluten with an effective amount of nepenthesin or a derivative thereof prior to consumption by the patient. In some embodiments, the food is combined with an effective amount of nepenthesin or a derivative thereof during its preparation, preferably after any heating steps.

In some embodiments, nepenthesin or a derivative thereof is administered as a food additive together with a food comprising gluten or suspected of comprising gluten, such as bread, pasta, cereal, and the like, made from wheat, rye and barley, etc. In some embodiments, nepenthesin or a derivative thereof is added as an ingredient in such food. In some embodiments, nepenthesin or a derivative thereof is dispersed into a food prior to consumption, optionally at a pH where it is inactive, such as a pH of about or above 5. In some embodiments, nepenthesin or a derivative thereof can be made or incorporated into a powder, a spread, a spray, a sauce, a dip, a whipped cream, etc., that can be applied to the gluten comprising food when the food is being consumed by a patient. In some embodiments, nepenthesin or a derivative thereof can be made into forms that appeal to one's appetite, such as candies, chewing gums, dietary supplement chews, syrup, etc. for easy administration. In some embodiments, nepenthesin or a derivative thereof can be mixed with common food items, such as sugar, salt, salad dressing, spices, cheese, butter, margarines, spreads, butter, frying shortenings, mayonnaises, dairy products, nut butters, seed butters, kernel butters, peanut butter, etc. Preferably, the food items or additives comprising nepenthesin do not require heating before being ingested by a patient so that possible loss of activity of nepenthesin or a derivative thereof due to elevated temperature can be minimized.

In another aspect, provided is a food product comprising nepenthesin or a derivative thereof. In some embodiments, the food product comprises gluten or is suspected of comprising gluten, such as bakery products (e.g., cakes, muffins, donuts, pastries, rolls, and bread), pasta, crackers, tortilla chips, cereal etc. made from wheat, rye and barley. In some embodiments, the food product can be consumed with another food product comprising gluten or suspected of comprising gluten. Non-limiting examples of such food include a powder, a spread, a spray, a sauce, a dip, a whipped cream, candies, chewing gums, syrup, sugar, salt, salad dressing, spices, cheese, butter, margarines, spreads, butter, frying shortenings, mayonnaises, dairy products, nut butters, seed butters, kernel butters, peanut butter, etc.

In some embodiments, the nepenthesin or derivative thereof is admixed with food, or used to pre-treat foodstuffs containing glutens. Nepenthesin present in foods can be enzymatically active to reduce the level of gluten in the food prior to or during ingestion.

In some embodiments, the composition (such as pharmaceutical composition or edible composition) or food product comprises from about 0.1% to about 99%, from about 0.5% to about 95%, from about 1% to about 95%, from about 5% to about 95%, from about 10% to about 90%, from about 20% to about 80%, from about 25% to about 75% of nepenthesin. In some embodiments, the nepenthesin in the composition (such as pharmaceutical composition or edible composition) or food product is about 0.01%, about 0.1%, about 0.5%, about 1%, about 5%, about 10%, about 20%, about 25%, about 30%, about 35%, about 40%, about 45%, about 50%, about 55%, about 60%, about 65%, about 70%, about 75%, about 80%, about 85%, about 90%, or about 95% of the total composition or food product, or a range between any two of the values (including end points).

In another aspect, provided is a composition for optimizing cleavage of a gluten protein at a proline residue, comprising a mixture of recombinant nepenthesin I and recombinant nepenthesin II. In one aspect, provided is a composition for optimizing cleavage of a gluten protein at a glutamine residue, comprising a mixture of recombinant nepenthesin I and recombinant nepenthesin II. In some embodiments, the composition is least about 20%, 50%, 2 times, 5, times or 10 times more effective in cleaving a gluten protein at a proline residue as compared to a composition comprising a same amount or concentration of either nepenthesin I or nepenthesin II alone. In some embodiments, the composition is least about 20%, 50%, 2 times, 5, times or 10 times more effective in cleaving a gluten protein at a glutamine residue as compared to a composition comprising a same amount or concentration of either nepenthesin I or nepenthesin II alone.

In another aspect, provided is a composition for optimizing cleavage of a protein at an amino acid residue(s), such as H, K, R, D, E, S, T, and/or N. In some embodiments, the composition is least about 20%, 50%, 2 times, 5 times or 10 times more effective in cleaving a protein at a given amino acid residue(s) as compared to a composition comprising a same amount or concentration of either nepenthesin I or nepenthesin II alone. In some embodiments, the composition is least about 10 times, 100 times, 500 times, 1000 times, 1400 times, or 2000 times or greater more effective in cleaving a protein at a given amino acid residue(s) as compared to a composition comprising a same amount or concentration of pepsin. In some embodiments, the residue is a residue that can be cleaved by pepsin. In some embodiments, the residue is a residue that is not efficiently cleaved by pepsin.

In another aspect, provided is a composition comprising fragmented gluten, wherein the composition is enriched in gluten fragments produced by cleavage of the gluten at a proline residue of the gluten. In one aspect, provided is a composition comprising fragmented gluten, wherein composition is enriched in gluten fragments produced by cleavage of the gluten at a glutamine residue. In some embodiments, the gluten fragments produced by cleavage of the gluten at a proline residue of the gluten is least 2 times, 5 times, or 10 times of the gluten fragments produced by cleavage of the gluten at a proline residue of the gluten by a composition comprising a same amount or concentration of either nepenthesin I or nepenthesin II alone. In some embodiments, the gluten fragments produced by cleavage of the gluten at a glutamine residue of the gluten is least 2 times, 5 times, 10 times of the gluten fragments produced by cleavage of the gluten at a glutamine residue of the gluten by a composition comprising a same amount or concentration of either nepenthesin I or nepenthesin II alone.

In another aspect, provided is a composition for optimizing cleavage of a protein at other amino acid residue(s), such as H, K, R, D, E, S, T, and/or N. In some embodiments, the protein fragments produced by cleavage of the protein at a given amino acid residue(s) of the protein is least 2 times, 5 times, or 10 times of the protein fragments produced by cleavage of the protein at the given amino acid residue(s) of the protein by a composition comprising a same amount or concentration of either nepenthesin I or nepenthesin II alone. In some embodiments, the protein fragments produced by cleavage of the protein at a given amino acid residue(s) of the protein is least about 10 times, 50 times, 500 times, 1000 times, 1400 times, or 2000 times or greater of the protein fragments produced by cleavage of the protein at the given amino acid residue(s) of the protein by a composition comprising a same amount or concentration of pepsin. In some embodiments, the residue is a residue that can be cleaved by pepsin. In some embodiments, the residue is a residue that is not efficiently cleaved by pepsin.

Methods of Preparation

Nepenthesin can be concentrated (or extracted) or purified by known methods, such as filtration or affinity purification based on immobilized pepstatin, from a natural source, such as pitcher secretions of plants such as *Nepenthes*. Nepenthesin I and II are found in relatively small quantity in natural plant secretions. Production of nepenthesin I and/or nepenthesin II can be increased, for example, using bioengineering technologies to create transgenic plants that express and/or secrete increased amounts of nepenthesin I or nepenthesin II, or a derivative thereof.

Besides being isolated from a plant source, nepenthesin such as nepenthesin I and/or nepenthesin II or a derivative thereof may be prepared by chemical synthesis. Chemical synthesis can be achieved by coupling of the amino acids according to the sequence of nepenthesin. Various peptide coupling methods and commercial peptide synthetic apparatuses are available to synthesis peptide or proteins, for example, automated synthesizers by Applied Biosystems, Inc., Foster City, Calif., Beckman, and other manufacturers.

In another aspect, provided is a method of preparing nepenthesin using recombinant production systems by transforming or transfecting a cell with the DNA and/or messenger RNA of nepenthesin so that the cell is capable of producing nepenthesin. For example, nepenthesin can be produced by establishing host-vector systems in organisms such as *Escherichia coli, Saccharomyces cerevisiae, Pichia pastoris, Lactobacillus*, Bacilli, Aspergilli, and plant cell cultures, such as tobacco cells, etc.

Vectors and host cells, such as *E. coli*, comprising polynucleotides and compositions containing any of the polynucleotides or polypeptides are also provided.

In another aspect, provided is a method for producing recombinant nepenthesin such as nepenthesin I and/or nepenthesin II or a derivative thereof comprising expressing in a chosen host organism a nucleic acid sequence which encodes said nepenthesin or homologue thereof, and inserting the nucleic acid sequence into an appropriately designed vector. In one aspect, the recombinant nepenthesin is nepenthesin I or a derivative thereof. In one aspect, the recombinant nepenthesin is nepenthesin II or a derivative thereof. In one aspect, the recombinant nepenthesin is a mixture of nepenthesin I and nepenthesin II or derivatives thereof.

In another aspect, provided is a composition comprising recombinant nepenthesin such as nepenthesin I and/or nepenthesin II or a derivative thereof. In one aspect, the recombinant nepenthesin is nepenthesin I or a derivative thereof. In one aspect, the recombinant nepenthesin is nepenthesin II or a derivative thereof. In one aspect, the recombinant nepenthesin is a mixture of nepenthesin I and nepenthesin II or derivatives thereof.

Nepenthesin has two known isoforms: nepenthesin I (known to have two variants nepenthesin Ia and nepenthesin Ib) and II. The sequences of nepenthesin and the nucleotide sequencing of the cDNA encoding nepenthesin are known in the art, for example, described in Athauda S B et al., Enzymic and structural characterization of nepenthesin, a unique member of a novel subfamily of aspartic proteinases, *Biochem. J.* 381:295-306 (2004). Nepenthesin I mRNA sequences have been described from several species, for example, *Nepenthes mirabilis* (GenBank Accession No. JX494401), *Nepenthes gracilis* (GenBank Accession No. AB114914), and *Nepenthes alata* (GenBank Accession No. AB266803). Nepenthesin II mRNA sequences have been described from several species, for example, *Nepenthes mirabilis* (GenBank Accession No. JX494402), *Nepenthes gracilis* (GenBank Accession No. AB114915), and *Zea mays* (GenBank Accession No. NM_001147869). Nepenthesin I protein sequences have been described from several species, for example, *Nepenthes mirabilis* (GenBank Accession No. AFV26024), *Nepenthes gracilis* (GenBank Accession No. BAD07474), *Nepenthes alata* (GenBank Accession No. BAF98915), and *Zea mays* (NCBI Reference Sequence: NP 001150925). Nepenthesin II protein sequences have been described from several species, for example, *Nepenthes mirabilis* (GenBank Accession No. AFV26025), *Nepenthes gracilis* (GenBank Accession No. BAD07475), and *Zea mays* (NCBI Reference Sequence: NP 001149229). A putative nepenthesin I protein has been described for *Oryza sativa* (GenBank Accession No. BAD38020). A putative nepenthesin II protein has been described for *Oryza sativa* (GenBank Accession No. BAD82000).

Sequence alignment of the known nepenthesin proteins (and putative proteins) is shown in FIG. 9, with corresponding pairwise alignment scores in Table 1. A phylogenetic tree representing the data is shown in FIG. 10. Athauda, et al. further compare nepenthesins with related typical aspartic proteases. Athauda, et al. predicted the backbone structure of nepenthesin Ia based on the structure of porcine pepsin A (nepenthesin Ib and II were predicted to be essentially the same as nepenthesin Ia). The putative catalytic aspartic acid residues were conserved based on this analysis.

In some embodiments, biosynthesis of nepenthesin can be achieved by transforming a cell with a vector comprising a cDNA that encodes nepenthesin I, for example the nucleotide sequence of SEQ ID NO. 1, GenBank Accession No. JX494401, GenBank Accession No. AB114914, or GenBank Accession No. AB266803. In some embodiments, biosynthesis of nepenthesin can be achieved by transforming a cell with a vector comprising a sequence homologous to a cDNA which encodes nepenthesin I, which sequence encodes a protein with protease activity. The sequence may have at least about 60% homology to a cDNA that encodes nepenthesin I. The sequence may have at least about 70% homology to a cDNA that encodes nepenthesin I. The sequence may have at least about 80% homology to a cDNA that encodes nepenthesin I. The sequence may have at least about 85% homology to a cDNA that encodes nepenthesin I. The sequence may have at least about 90% homology to a cDNA that encodes nepenthesin I. The sequence may have at least about 95% homology to a cDNA that encodes nepenthesin I. The sequence may have at least about 96% homology to a cDNA that encodes nepenthesin I. The sequence may have at least about 97% homology to a cDNA that encodes nepenthesin I. The sequence may have at least about 98% homology to a cDNA that encodes nepenthesin I. The sequence may have at least about 99% homology to a cDNA that encodes nepenthesin I.

In some embodiments, biosynthesis of nepenthesin can be achieved by transforming a cell with a vector comprising a cDNA that encodes nepenthesin II, for example the nucleotide sequence of GenBank Accession No. JX494402 or GenBank Accession No. AB114915. In some embodiments, biosynthesis of nepenthesin can be achieved by transforming a cell with a vector comprising a sequence homologous to a cDNA which encodes nepenthesin II, which sequence encodes a protein with protease activity. The sequence may have at least about 60% homology to a cDNA that encodes nepenthesin II. The sequence may have at least about 70% homology to a cDNA that encodes nepenthesin II. The sequence may have at least about 80% homology to a cDNA that encodes nepenthesin II. The sequence may have at least about 85% homology to a cDNA that encodes nepenthesin II. The sequence may have at least about 90% homology to a cDNA that encodes nepenthesin II. The sequence may have at least about 95% homology to a cDNA that encodes nepenthesin II. The sequence may have at least about 96% homology to a cDNA that encodes nepenthesin II. The sequence may have at least about 97% homology to a cDNA that encodes nepenthesin II. The sequence may have at least about 98% homology to a cDNA that encodes nepenthesin II. The sequence may have at least about 99% homology to a cDNA that encodes nepenthesin II.

The synthetic nepenthesin such as nepenthesin I and/or nepenthesin II or a derivative thereof can be concentrated or purified according to known methods, such as those for isolating nepenthesin or a derivative thereof from the plant pitcher liquid.

In some embodiments, the protein product isolated from a natural source or a synthetic source comprises at least 20% by weight of nepenthesin or a derivative thereof. In some embodiments, the isolated protein product comprises at least about 50%, about 75%, about 90%, about 95% by weight of nepenthesin or a derivative thereof. In some embodiments, the isolated protein product comprises at least 99% by weight of nepenthesin or a derivative thereof.

In some embodiments, the recombinant nepenthesin comprises substantially only nepenthesin I. In some embodiments, the recombinant nepenthesin comprises substantially only nepenthesin II. In some embodiments, the recombinant nepenthesin comprises a ratio of nepenthesin I to nepenthesin II of at least about 100:1. In some embodiments, the recombinant nepenthesin comprises a ratio of nepenthesin I to nepenthesin II of at least about 90:1. In some embodiments, the recombinant nepenthesin comprises a ratio of nepenthesin I to nepenthesin II of at least about 70:1. In some embodiments, the recombinant nepenthesin comprises a ratio of nepenthesin I to nepenthesin II of at least about 60:1. In some embodiments, the recombinant nepenthesin comprises a ratio of nepenthesin I to nepenthesin II of at least about 50:1. In some embodiments, the recombinant nepenthesin comprises a ratio of nepenthesin I to nepenthesin II of at least about 40:1. In some embodiments, the recombinant nepenthesin comprises a ratio of nepenthesin I to nepenthesin II of at least about 30:1. In some embodiments, the recombinant nepenthesin comprises a ratio of nepenthesin I to nepenthesin II of at least about 20:1. In some embodiments, the recombinant nepenthesin comprises a ratio of nepenthesin I to nepenthesin II of at least about 10:1. In some embodiments, the recombinant nepenthesin comprises a ratio of nepenthesin I to nepenthesin II of at least about 5:1. In some embodiments, the recombinant nepenthesin comprises a ratio of nepenthesin I to nepenthesin II of at least about 4:1. In some embodiments, the recombinant nepenthesin comprises a ratio of nepenthesin I to nepenthesin II of at least about 3:1. In some embodiments, the recombinant nepenthesin comprises a ratio of nepenthesin I to nepenthesin II of at least about 2:1. In some embodiments, the recombinant nepenthesin comprises a ratio of nepenthesin I to nepenthesin II of at least about 1:1. In some embodiments, the recombinant nepenthesin comprises a ratio of nepenthesin I to nepenthesin II of at least about 1:2. In some embodiments, the recombinant nepenthesin comprises a ratio of nepenthesin I to nepenthesin II of at least about 1:3. In some embodiments, the recombinant nepenthesin comprises a ratio of nepenthesin I to nepenthesin II of at least about 1:4. In some embodiments, the recombinant nepenthesin comprises a ratio of nepenthesin I to nepenthesin II of at least about 1:5. In some embodiments, the recombinant nepenthesin comprises a ratio of nepenthesin I to nepenthesin II of at least about 1:10. In some embodiments, the recombinant nepenthesin comprises a ratio of nepenthesin I to nepenthesin II of at least about 1:20. In some embodiments, the recombinant nepenthesin comprises a ratio of nepenthesin I to nepenthesin II of at least about 1:30. In some embodiments, the recombinant nepenthesin comprises a ratio of nepenthesin I to nepenthesin II of at least about 1:40. In some embodiments, the recombinant nepenthesin comprises a ratio of nepenthesin I to nepenthesin II of at least about 1:50. In some embodiments, the recombinant nepenthesin comprises a ratio of nepenthesin I to nepenthesin II of at least about 1:60. In some embodiments, the recombinant nepenthesin comprises a ratio of nepenthesin I to nepenthesin II of at least about 1:70. In some embodiments, the recombinant nepenthesin comprises a ratio of nepenthesin I to nepenthesin II of at least about 1:80. In some embodiments, recombinant nepenthesin comprises a ratio of nepenthesin I to nepenthesin II of at least about 1:90. In some embodiments, the recombinant nepenthesin comprises a ratio of nepenthesin I to nepenthesin II of at least about 1:100.

In some embodiments, the protein product isolated from a natural source or a synthetic source comprises a protein that is at least about 70% homologous to nepenthesin I and retains protease activity. The protein may be at least about 80% homologous to nepenthesin I. The protein may be at least about 85% homologous to nepenthesin I. The protein may be at least about 90% homologous to nepenthesin I. The protein may be at least about 95% homologous to nepenthesin I. The protein may be at least about 96% homologous to nepenthesin I. The protein may be at least about 97% homologous to nepenthesin I. The protein may be at least about 98% homologous to nepenthesin I. The protein may be at least about 99% homologous to nepenthesin I.

In some embodiments, the protein product isolated from a natural source or a synthetic source comprises a protein that is at least about 70% homologous to nepenthesin II and retains protease activity. The protein may be at least about 80% homologous to nepenthesin II. The protein may be at least about 85% homologous to nepenthesin II. The protein may be at least about 90% homologous to nepenthesin II. The protein may be at least about 95% homologous to nepenthesin II. The protein may be at least about 96% homologous to nepenthesin II. The protein may be at least about 97% homologous to nepenthesin II. The protein may be at least about 98% homologous to nepenthesin II. The protein may be at least about 99% homologous to nepenthesin II.

In some embodiments, the protein product isolated from a natural source or a synthetic source comprises nepenthesin or a derivative thereof with at least about 10% of the original protease activity of nepenthesin I. In some embodiments, the protein product comprises nepenthesin or a derivative thereof with at least about 20% of the original protease activity of nepenthesin I. In some embodiments, the protein product comprises nepenthesin or a derivative thereof with at least about 30% of the original protease activity of nepenthesin I. In some embodiments, the protein product comprises nepenthesin or a derivative thereof with at least about 40% of the original protease activity of nepenthesin I. In some embodiments, the protein product comprises nepenthesin or a derivative thereof with at least about 50% of the original protease activity of nepenthesin I. In some embodiments, the protein product comprises nepenthesin or a derivative thereof with at least about 60% of the original protease activity of nepenthesin I. In some embodiments, the protein product comprises nepenthesin or a derivative thereof with at least about 70% of the original protease activity of nepenthesin I. In some embodiments, the protein product comprises nepenthesin or a derivative thereof with at least about 80% of the original protease activity of nepenthesin I. In some embodiments, the protein product comprises nepenthesin or a derivative thereof with at least about 90% of the original protease activity of nepenthesin I. In some embodiments, the protein product comprises nepenthesin or a derivative thereof with greater than about 100% of the original protease activity of nepenthesin I.

In some embodiments, the protein product isolated from a natural source or a synthetic source comprises nepenthesin or a derivative thereof with at least about 10% of the original protease activity of nepenthesin II. In some embodiments, the protein product comprises nepenthesin or a derivative thereof with at least about 20% of the original protease activity of nepenthesin II. In some embodiments, the protein product comprises nepenthesin or a derivative thereof with at least about 30% of the original protease activity of nepenthesin II. In some embodiments, the protein product comprises nepenthesin or a derivative thereof with at least about 40% of the original protease activity of nepenthesin II. In some embodiments, the protein product comprises nepenthesin or a derivative thereof with at least about 50% of the original protease activity of nepenthesin II. In some embodiments, the protein product comprises nepenthesin or a derivative thereof with at least about 60% of the original protease activity of nepenthesin II. In some embodiments, the protein product comprises nepenthesin or a derivative thereof with at least about 70% of the original protease activity of nepenthesin II. In some embodiments, the protein product comprises nepenthesin or a derivative thereof with at least about 80% of the original protease activity of nepenthesin II. In some embodiments, the protein product comprises nepenthesin or a derivative thereof with at least about 90% of the original protease activity of nepenthesin II. In some embodiments, the protein product comprises nepenthesin or a derivative thereof with greater than about 100% of the original protease activity of nepenthesin II.

III. Examples

Unless stated otherwise, the abbreviations used throughout the specification have the following meanings:

g=gram
kDa=kiloDalton
kg=kilogram
L=liter
LC=liquid chromatography
mg=milligram
min=minute
mL=milliliter
mM=millimolar
MS=mass spectrometry
nM=nanomolar
pM=picomolar
s.d.=standard deviation
µCi=microcurie
µg microgram
µL=microliter
µM=micromolar
µm=micrometer
° C.=degree Celsius These one-letter symbols have the following meaning when representing amino acids:

A=Alanine
R=Arginine
N=Asparagine
D=Aspartic acid
C=Cysteine
E=Glutamic acid
Q=Glutamine
G=Glycine
H=Histidine
I=Isoleucine
L=Leucine
K=Lysine
M=Methionine
F=Phenylalanine
P=Proline
S=Serine
T=Threonine
W=Tryptophan
Y=Tyrosine
V=Valine

Example 1

Nepenthesin Extract Preparation

Chemicals

Water and acetonitrile, HPLC grade form Burdick and Jackson, were purchased from VWR. Formic acid, Tris, glycine were purchased from Sigma Aldrich.

Plant Culture

Transplants of *Nepenthes rafflesiana, Nepenthes ampularia, Nepenthes mirabilis*, and *Nepenthes globosa* were purchased from Keehns Carnivores (accessible via hypertext transfer protocol on the world wide web at keehnscarnivores.ca). These were potted with wood bark, perlite, peat moss and humus (40, 35, 10, 5% respectively). Growth conditions involved 14 hours of light per day, 80% humidity and temperature in the 23-28° C. range with 2 to 3 waterings a week. Upon pitcher maturity, plants were fed with one or two *Drosophila* per pitcher and the pitcher fluid harvested one week later. Pitchers and their secretions were left to recover for one week prior to a second round of feeding and extraction.

Extract Preparation

Pitcher fluid was collected from all four species of plants and combined. The crude pitcher fluid was first clarified through a 0.22 µm filter, then concentrated 80 to 100 fold using an Amicon Ultra centrifugal 10 kDa molecular weight cut-off filter (both from Millipore). Prior to use in digestions, the concentrate was acid-activated with 100 mM Glycine HCl (pH 2.5) for 3 hours, then washed 3× with 100 mM Glycine-HCl (pH 2.5) in the filtration device, using 10× fluid volume for each wash). The final isolate was then rediluted to an 11× concentration based on the original sampling of pitcher fluid.

Characterization of Pitcher Fluid Extract

The fluidic secretions of the pitcher plant were concentrated and the digestion enzymes activated by pH reduction (pH 2.5). The impact of the enrichment process and the activation on the fluid proteome was determined using proteomics methods. First, to confirm the presence of nepenthesin enzyme, the inactive concentrate was separated by SDS-PAGE. Seven contiguous gel zones with very faint coomassie staining were digested with trypsin and analyzed by nanoLC-MS/MS using standard methods. This is not expected to be a complete catalog of the activated fluid proteome, but the analysis confirmed the presence of the aspartic protease nepenthesin I/II, as well as a glucanase, chitinase, carboxypeptidase and peroxidase of plant origin, plus modest levels of *drosophila* and bacterial contamination. The low complexity of the fluid proteome is consistent with recent analyses, Hatano N, Hamada T (2012) Proteomic analysis of secreted protein induced by a component of prey in pitcher fluid of the carnivorous plant *Nepenthes alata. Journal of Proteomics* 3; 75(15):4844-52 (Epub Jun. 15, 2012), but nepenthesin-I was found distributed over a much wider mass range in this analysis (40-70 kDa). The acid-activated fluid was then processed and analyzed in a similar fashion. The activation process reduced the overall protein yield, and also appeared to simplify the composition. Aside from nepenthesin-I, only minor contamination from keratin and actin were in evidence. These analyses point to the low complexity of the enriched fluid, where nepenthesin is the major component. The total protein concentration of the activated and 80× enriched fluid was measured by a BCA assay to be 22 ng/µL. This value is consistent with an earlier study describing enrichment of the fluid. Tokes Z A, et al., Digestive Enzymes Secreted by Carnivorous Plant *Nepenthes*-Macferlanei-L. *Planta* 119(1):39-46 (1974).

Example 2

Digest Mapping of Proteins by Pepsin and Nepenthesin Extract

Nepenthesin Digest Mapping by Mass Spectrometry

Nepenthesin extract was prepared as in Example 1.

Digestions of proteins were carried out in solution using a LEAP HTX-PAL autosampler and dispensing system designed for hydrogen/deuterium exchange (HDX) applications, and data were collected with an AB Sciex Triple-TOF 5600 QqTOF mass spectrometer. Peptides were identified using Mascot (v2.3) from MS/MS data. Briefly, 8 µL, of 8 µM protein (XRCC4, XLF, Ligase IV-tandem BRCT domains, PNK, myoglobin, or cytochrome C) were mixed with 10 µL of 11× concentrated fluid for 2 min. at 10° C. Myoglobin and cytochrome C were purchased from Sigma. After dilution to 1 µM substrate concentration, 15 µL were injected into the chilled reversed-phase LC system (4° C.) connected to the mass spectrometer. The peptides were trapped on a 5 cm, 200 µm i.d. Onyx C18 monolithic column (Phenomenex Inc.) and eluted with an acetonitrile gradient from 3% to 40% in 10 minutes. Peptides detected in these analyses were selected for CID fragmentation in multiple information-dependent acquisitions of MS/MS spectra, akin to the gas-phase fractionation strategy. Blonder J, et al., Proteomic investigation of natural killer cell microsomes using gas-phase fractionation by mass spectrometry. *Biochimica Et Biophysica Acta—Proteins and Proteomics* 1698(1):87-95 (2004). Spectra were searched against a miniature database containing the sequences for all six proteins. Sequencing results were manually verified.

Results

A series of proteins were digested with the enriched fluid under conditions suitable for HDX-MS experiments. The digestion specificity of the concentrate was characterized at the P1 and P1' positions (FIG. 1), to support a comparison with similar studies applied to pepsin. Hamuro Y, et al., Specificity of immobilized porcine pepsin in H/D exchange compatible conditions. *Rapid Communications in Mass Spectrometry* 22(7):1041-1046 (2008). In this example, the enzyme-to-substrate ratio was 1:85 based on the assumption that all the measured protein in the enriched fluid is nepenthesin, even though some contaminating proteins were obviously present.

The nepenthesin data represents an assessment of 1612 residues and although not as extensive as the corresponding pepsin data (13,766 residues), the sequence diversity is sufficiently high in the protein set to warrant a comparison at the level of P1 and P1' positions. The greatest specificity for pepsin appears to be in the P1 position. It presents high-efficiency cleavage for the hydrophobic residues F, L and M but cleavage after P, H, K and R is essentially forbidden. Nepenthesin cleaves after most residues with the exception of G, S, T, V, I and W. It supports a high rate of cleavage after the expected pepsin P1 residues but also at the residues forbidden in pepsin digestion, notably K, R and P. In the P1' position, pepsin shows a preference for hydrophobic residues in general, including any residue with aromaticity. Conversely, nepenthesin demonstrates little in the way of selectivity at the P1' position, except perhaps against G, P and H. Overall, nepenthesin demonstrates significantly relaxed specificity at the P1 position relative to pepsin, and provides an indication of very high efficiency.

Example 3

Digest Mapping of Multi-Domain Protein, XRCC4, by Pepsin and Nepenthesin Extract HD Exchange of a Complex Involved in DNA-Damage Repair Nepenthesin extract was prepared as in Example 1.

Stock solutions of XRCC4 (1-200) with BRCT, and XRCC4 (full length) with BRCT were diluted in buffer (10 mM Tris-HCl, pH 7.5) to equimolar concentrations (10 µM) and incubated at 4° C. for a minimum of 30 min to promote complexation. The samples were held at 4° C. until HDX analysis. Aliquots were deuterated for 2 min at 20° C. with the addition of $D_2O$ (25% v/v). Aliquots were then digested in two ways. In the first digestion strategy, protein deuteration was quenched by adding the sample to chilled 100 mM glycine-HCl (pH 2.5), and the quenched protein solution was injected into a pepsin microreactor. This microreactor was installed in the HTX-PAL system between the injector valve and the C18 column. Protein digest was captured on the monolithic C18 capillary column and eluted into the mass spectrometer. All fluidic elements, including the microreactor, were chilled at 4° C. to minimize deuterium back-exchange during the analysis time (<15 min). In the second digestion strategy, an equivalent amount of deuterated protein was simultaneously quenched and digested with 3 or 5 µL of 11× nepenthes fluid for 3 or 5 min, respectively, at 10° C. The sample was injected into the chilled LC-system connected to the mass spectrometer.

Replicate mass shift measurements were made (4 or more) and referenced to control protein states—free XRCC4 (1-200), free XRCC4 (full length) and free LigIV-BRCT. The average deuterium level for each peptide was determined using Mass Spec Studio (manuscript in preparation), which is a rebuild of Hydra v1.5. Slysz G W, et al., Hydra: software for tailored processing of H/D exchange data from MS or tandem MS analyses. *Bmc Bioinformatics* 10 (2009). Perturbations in mass shifts were considered significant if (a) they passed a two-tailed t test (p<0.05) using pooled standard deviations from the analyses of each state, (b) they passed a distribution analysis to guard against spectral overlap and (c) they exceeded a threshold shift value (±2 s.d.) based on a measurement of the shift noise and assuming its normal distribution Bennett M J, et al., Discovery and Characterization of the Laulimalide-Microtubule Binding Mode by Mass Shift Perturbation Mapping. *Chemistry & Biology* 17(7):725-734 (2010).

Results

To determine if relaxed specificity translates into an improvement in sequence mapping for HDX-MS applications, full-length XRCC4, a protein that contains a globular domain, and extended helical stalk, and a long disordered C-terminal was profiled. Hammel M, et al., XLF Regulates Filament Architecture of the XRCC4. Ligase IV Complex. *Structure* 18(11):1431-1442 (2010); and Junop M S, et al., Crystal structure of the Xrcc4 DNA repair protein and implications for end joining. *Embo J* 19(22):5962-5970 (2000). Such multi-domain proteins are challenging to encompass in a single digestion protocol, and in particular, intrinsically-disordered regions tend to digest poorly with pepsin as they are relatively depleted in hydrophobic residues and enriched in proline and charged residues. Dunker A K, et al. Intrinsically disordered protein. *Journal of*

Figure 2A:
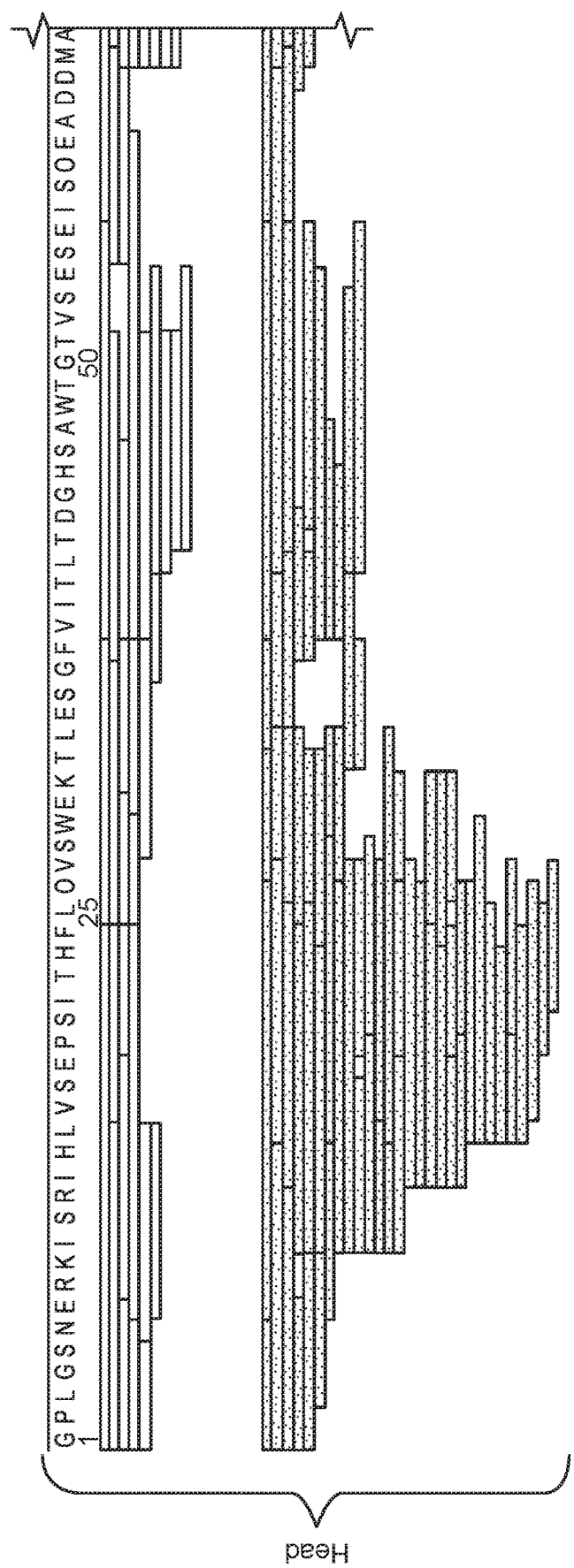
Figure 2B:
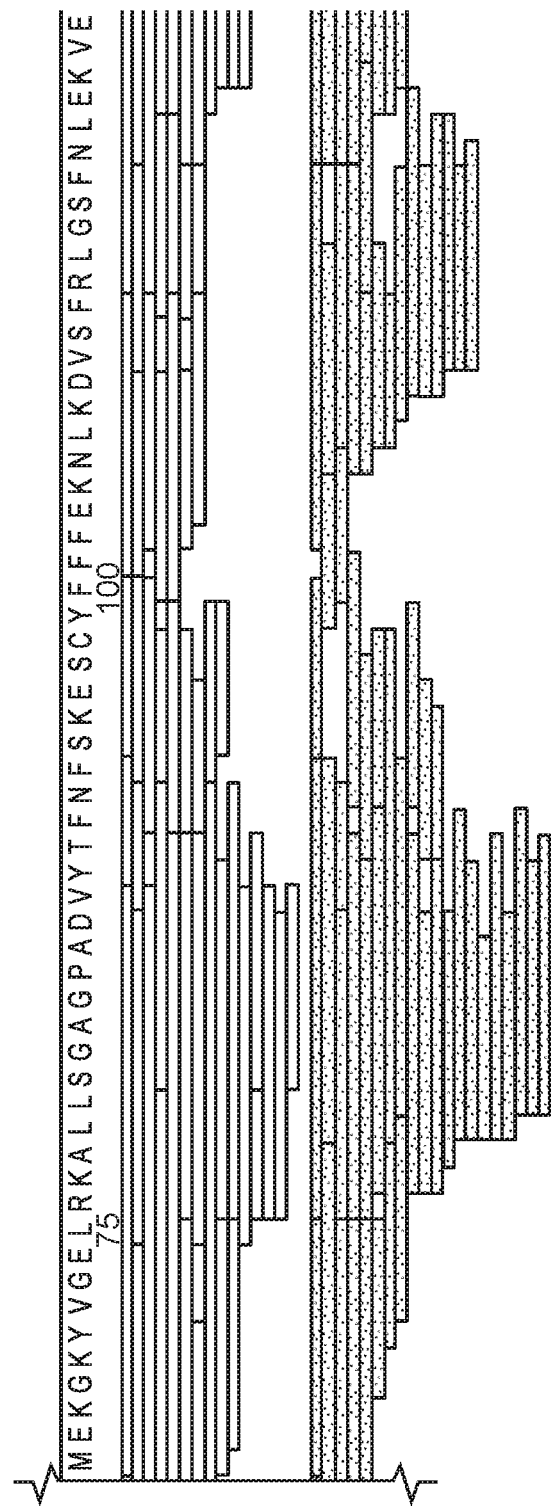
Figure 2C:
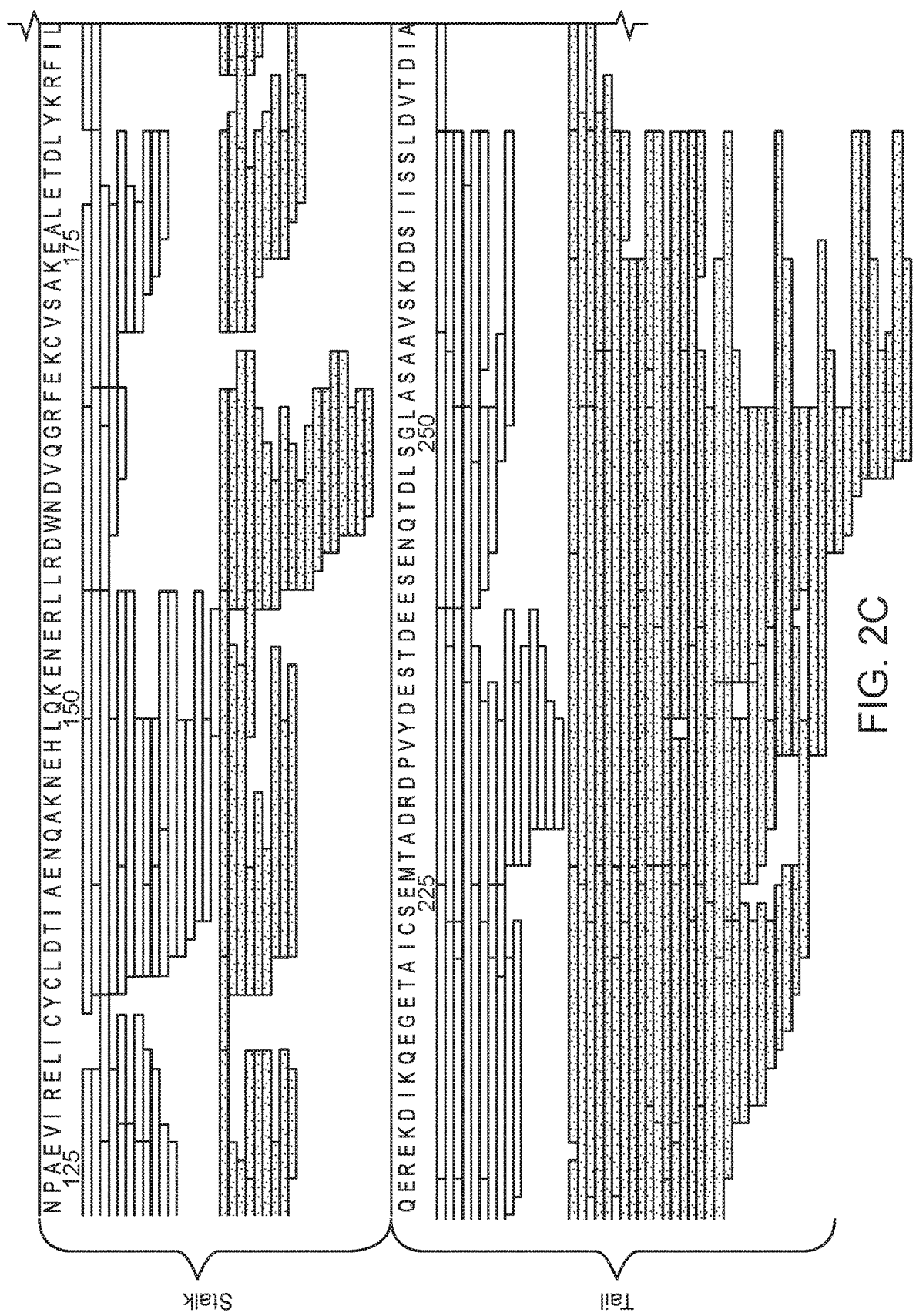
Figure 2D:
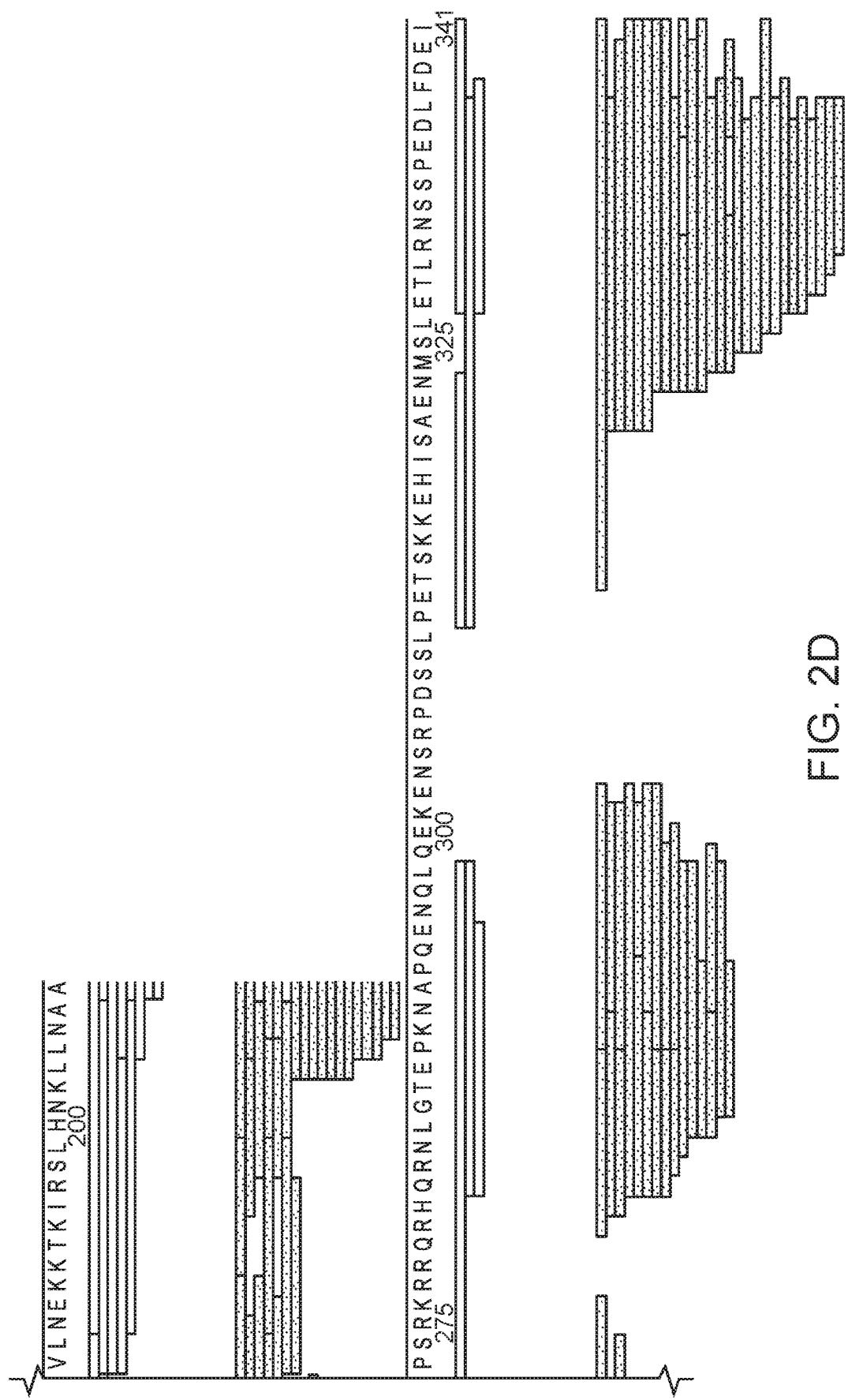

*Molecular Graphics & Modelling* 19(1):26-59 (2001). The pepsin and nepenthesin maps for this protein are displayed in FIG. 2. In this comparison, an exhaustive mapping was pursued for both enzymes, using a range of different protease amounts, and recursive MS/MS experiments. Nepenthesin provides superior coverage of the full length protein: 357 peptides for nepenthesin (hatched bars) compared to 187 for pepsin (white bars). (The average peptide length of 11 residues was the same for both enzymes.) Both enzymes represent the globular and stalk regions with a large number of overlapping peptides but the complementarity provided by nepenthesin is evident. For example, nepenthesin offers considerably deeper coverage of a β-sheet region in the globular domain (residues 1-30, FIG. 2A). The disordered C-terminal region is covered to a much greater extent as well, and to a considerably higher level of redundancy (FIG. 2C-D). Each residue in this disordered tail region receives 16× coverage using nepenthesin and only 4.7× coverage with pepsin.

The existence of any bias in peptide detection is explored by selecting average search score as the metric (FIG. 3). The approach emphasizes confidence in sequence identification as the principle means by which sequence maps are defined. One outliner is R. The higher scores for peptides terminating in R likely reflect a combination of higher average peptide intensity and better fragmentation, which is consistent with what we know from trypsin-based bottom-up proteomics. Warwood S, et al. Guanidination chemistry for qualitative and quantitative proteomics. *Rapid Communications in Mass Spectrometry* 20(21):3245-3256 (2006).

Example 4

Digestion of XRCC4 with Varying Enzyme-to-Substrate Ratios

The enzyme efficiency was examined in greater detail. The degree to which the peptide mass map could be varied, or tuned, simply by altering the enzyme-to-substrate ratio is shown in FIG. 4. Nepenthesin load was varied over a 50-fold range for in-solution digestions. For the pepsin experiment, immobilized pepsin in a slurry format was used rather than free pepsin to avoid extensive pepsin autolysis. The enzyme load was varied over an 8-fold range; lower amounts led to poor peptide intensities and higher amounts had no effect on the map. It was found that nepenthesin generated a very low autolysis profile even at the higher loads. An aggregate peptide ion chromatogram (PIC) was used as a measure of effective digestion. The comparison of the relatively similar distributions found at 0.38:1 (nepenthesin:substrate) with 520:1 (pepsin:substrate) represents a remarkable 1400-fold improvement in efficiency for nepenthesin over pepsin in HDX-like applications.

The nepenthesin digest could be more readily tuned from large fragments to small by varying the enzyme load, and generating a variable representation of XRCC4. This is demonstrated in FIG. 4A by the transition in the PIC from long retention times at low load to short retention times at high load. This transition correlated with the average peptide length for the most abundant peptides shifting from >12 at low enzyme load to 10 at high enzyme load. Conversely, varying pepsin load did not significantly alter the PIC or average peptide length (FIG. 4B). A forced-flow pepsin microreactor may improve tuning but would likely not generate smaller fragments.

Example 5

Digestion of Gliadin by Nepenthesin Extract

Digestions of gliadin by nepenthesin were performed in solution using a LEAP HTX-PAL autosampler and dispensing system designed for hydrogen/deuterium exchange (HDX) applications. Data were collected using an AB Sciex Triple-TOF 5600 QqTOF mass spectrometer. Peptides were identified using Mascot (v2.3) from MS/MS data. Briefly, 12 pmol of crude gliadin (purchased from Sigma Aldrich) were mixed with 2 µL of 100× concentrated extract, produced as described in Example 1. After digestion the entire volume was injected into a reversed-phase LC system connected to the mass spectrometer. The peptides were trapped on a 7 cm, 150 µm i.d. Magic C18 column and eluted with an acetonitrile gradient from 10% to 40% in 10 or 30 minutes. Peptides detected in these analyses were selected for CID fragmentation in multiple information-dependent acquisitions of MS/MS spectra. Spectra were searched against a miniature database containing the sequences for all identified wheat gliadin (α, β, γ, ω) proteins plus the low and high molecular weight glutenin. FIG. 5 shows the average length of all peptides identified from the nepenthesin digestion of gliadin from wheat, using LC-MS/MS, after 1, 5, 10, 15, 30, 60, 130, 360 or 810 minutes at 37° C. A 95% confidence cut-off ($p<0.05$) on the scores were used to remove false positive identification. Relative standard deviation of the peptide length is shown in the inset figure.

FIG. 6 displays the number of peptides identified by LC-MS/MS after 1, 5, 10, 15, 30, 60, 130, 360 or 810 minutes digestion at 37° C., grouped by length. Data as in FIG. 5.

FIG. 7 displays the same data as in FIG. 5, as a probability of obtaining a certain length after 10, 60, 120, 360 or 810 minutes digestion at 37° C.

Example 6

Nepenthesin Extract Purification

Purification of Extract

Sepharose-immobilized pepstatin in a 50×2 cm ID column was equilibrated in 20 mM Glycine-HCl, pH 2.5-3. The filtered pitcher fluid (prepared as described in Example 1) was cycled twice through the column, and the column washed with 100 mL equilibration buffer (20 mM glycine HCl, pH 2.5). The column was eluted with 100 mM ammonium bicarbonate pH 8.7 and fractions collected. In order to preserve maximum the enzyme activity, the pH was decreased to 4 right after fraction collection with 2 M glycine HCl, pH 2.5. Activity was verified using a digestion assay, and the most active fractions combined and concentrated to approximately 80×, based on original fluid volume.

Example 7

Recombinant Nepenthesin I

The gene for nepenthesin I (see SEQ ID NO: 1; encoding amino acid residues 20-413, from *N. gracilis*, without the plant signal sequence) was prepared from nepenthesin I cDNA, and placed between NdeI and HindIII restriction sites. This sequence was cloned into pET21a, using T4 DNA ligase (1 U) (New England Bio, NEB), T4 DNA ligase buffer (NEB), ATP (0.5 mM) (NEB), 0.5 µg pET21a vector and 2 µg of the nepenthesin I cDNA. This was incubated at 18° C.

for 4 hours. The ligation mixture (5 µL) was added to 200 µL of NovaBlue competent cells and incubated on ice for 15 minutes. Cells were transformed by heat shock (45 seconds at 42° C., then immediately on ice, with 1 ml of LB medium) and incubated for 1 hour at 37° C., and plated with antibiotics (tetracycline and ampicillin). After confirming gene presence in several white colonies, a representative colony was chosen for maxiprep. The resulting recombinant plasmid pET21a/R.NepI was transformed into E. coli C41 by heat-shock as above, for expression under induction by IPTG. Here, cells were grown up to an $OD_{660}$ of 0.6 and induced with 0.1 mM IPTG for four hours at 37° C. The expressed protein went to inclusion bodies.

Inclusion bodies were isolated as follows. Cells were centrifuged, sucrose lysis buffer was added (25% saccharose, 50 mM TrisCl pH 7.4, 1 mM EDTA, 1 mM $NaN_3$, and protease inhibitors), and the cells were subjected to four rounds of freeze/thaw and sonication. This was followed by the addition of DNAse and RNAse for a 30 min. incubation at room temperature. The preparation was centrifuged (~15 min. at 5000×g) to pellet the inclusion bodies and membrane fragments. This pellet was resuspended in Triton buffer (50 mM TrisCl pH 7.4, 10 mM NaCl, 1 mM β-mercaptoethanol, 1 mM $NaN_3$, 0.5% Triton X100+protease inhibitors) and sonication performed on ice. This was once again centrifuged, to pellet the inclusion bodies, and the pellet was washed twice on ice (with mixing and sonication) in a buffer free of Triton (50 mM TrisCl pH 7.4, 10 mM NaCl, 1 mM β-mercaptoethanol, 1 mM $NaN_3$, protease inhibitors).

The protein pellet was then subjected to refolding. One g of inclusion bodies was suspended into 1 L of 50 mM CAPS pH 10.5, 8 M urea, 1 mM EDTA, 1 mM glycine, 500 mM NaCl, 300 mM β-mercaptoethanol and shaken for 1 hr. The suspension was dialysed against 50 mM Tris, pH 11, twice for 1 hour at a time, followed by one day of dialysis against 50 mM Tris, pH 7.5, and finally, dialysis against phosphate buffer with 300 mM NaCl, pH 7.0.

The solution was centrifuged at high speed (10000×g for 15 min.) to remove any un-refolded protein, and the supernatant filtered through a 0.22 µm membrane. Nepenthesin I was activated at pH 2.5 (glycine-HCl) overnight at 4° C. Yields range from 10 to 100 mg of folded, activated protein, starting from 1 L of cell culture.

Example 8

Recombinant Nepenthesin II

The cDNA of nepenthesin II (from N. gracilis, without the plant signal sequence) was used to prepare nepenthesin II cDNA. This sequence was cloned into pET21a between NdeI and HindIII restriction sites, using T4 DNA ligase (1 U) (New England Bio, NEB), T4 DNA ligase buffer (NEB), ATP (0.5 mM) (NEB), 0.5 µg pET21a vector and 2 µg of the nepenthesin II cDNA. This was incubated at 18° C. for 4 hours. The ligation mixture (5 µL) was added to 200 µL of NovaBlue competent cells and incubated on ice for 15 minutes. Cells were transformed by heat shock (45 seconds at 42° C., then immediately on ice, with 1 ml of LB medium) and incubated for 1 hour at 37° C., and plated with antibiotics (tetracycline and ampicillin). After confirming gene presence in several white colonies, a representative colony was chosen for maxiprep. The resulting recombinant plasmid pET21a/R.NepI was transformed into E. coli C41 by heat-shock as above, for expression under induction by IPTG. Here, cells were grown up to an $OD_{660}$ of 0.6 and induced with 0.1 mM IPTG for four hours at 37° C. The expressed protein went to inclusion bodies.

Inclusion bodies were isolated as follows. Cells were centrifuged, sucrose lysis buffer was added (25% saccharose, 50 mM TrisCl pH 7.4, 1 mM EDTA, 1 mM $NaN_3$, and protease inhibitors), and the cells were subjected to four rounds of freeze/thaw and sonication. This was followed by the addition of DNAse and RNAse for a 30 min. incubation at room temperature. The preparation was centrifuged (~15 min. at 5000×g) to pellet the inclusion bodies and membrane fragments. This pellet was resuspended in Triton buffer (50 mM TrisCl pH 7.4, 10 mM NaCl, 1 mM β-mercaptoethanol, 1 mM $NaN_3$, 0.5% Triton X100+protease inhibitors) and sonication performed on ice. This was once again centrifuged, to pellet the inclusion bodies, and the pellet was washed twice on ice (with mixing and sonication) in a buffer free of Triton (50 mM TrisCl pH 7.4, 10 mM NaCl, 1 mM β-mercaptoethanol, 1 mM $NaN_3$, protease inhibitors).

The protein pellet was then subjected to refolding. One g of inclusion bodies was suspended into 1 L of 50 mM CAPS pH 10.5, 8 M urea, 1 mM EDTA, 1 mM glycine, 500 mM NaCl, 300 mM β-mercaptoethanol and shaken for 1 hr. The suspension was dialysed against 50 mM Tris pH 11 twice for 1 hour at a time, followed by one day of dialysis against 50 mM Tris pH 7.5, and finally, dialysis against phosphate buffer with 300 mM NaCl, pH 7.0.

The solution was centrifuged at high speed (10000×g for 15 min.) to remove any un-refolded protein, and the supernatant filtered through a 0.22 µm membrane. Nepenthesin II was activated at pH 2.5 (glycine-HCl) overnight at 4° C. Yields range from 10 to 100 mg of folded, activated protein, starting from 1 L of cell culture.

Example 9

Digest Mapping of Gliadin by Nepenthesin

Nepenthesin extract was prepared as described in Example 1. Purified nepenthesin extract was prepared as described in Example 6. Recombinant nepenthesin I was prepared as described in Example 7.

Gliadin digestion was performed as described in Example 5, except that the substrate to enzyme ratio was approximately 1000:1. Gliadin was digested at 37° C. for 2 hr with nepenthesin extract, purified nepenthesin extract, or recombinant nepenthesin I.

Gliadin is a class of proteins found in wheat and other cereal grains. Gliadins are highly enriched in proline and glutamine residues. We have determined that recombinant nepenthesin I digests gliadin protein very effectively at pH 2-3. The P1 cleavage preference of recombinant nepenthesin I is very similar to that of the concentrated fluid extract, as well as the purified fraction of the extract (FIG. 8A). Surprisingly, the extract showed a higher preference for glutamine than either the purified extract or recombinant nepenthesin I.

The P1 cleavage preference of recombinant nepenthesin I is very similar to that of the concentrated fluid extract, as well as the purified fraction of the extract (FIG. 8B). Surprisingly, the extract showed a higher preference for proline than either the purified extract or recombinant nepenthesin I.

The extract contains both nepenthesin I and II, but the purification strategy recovers far less active nepenthesin II than nepenthesin I. Without wishing to be bound by theory, it is believed that the heightened cleavage at the P1 glutamine position and the P1' proline position by the extract are due to nepenthesin II and/or to synergy between nepenthesin I and nepenthesin II.

Example 10

Comparison of Nepenthesin Proteins

The protein sequences of known and putative nepenthesin proteins were aligned using Clustal 2.1 Multiple Sequence Alignment. The sequences of nepenthesin I were: *Nepenthes mirabilis* (GenBank Accession No. AFV26024), *Nepenthes gracilis* (GenBank Accession No. BAD07474), *Nepenthes alata* (GenBank Accession No. BAF98915), *Zea mays* (NCBI Reference Sequence: NP 001150925), and *Oryza sativa* (GenBank Accession No. BAD38020). The sequences of nepenthesin II were: *Nepenthes mirabilis* (GenBank Accession No. AFV26025), *Nepenthes gracilis* (GenBank Accession No. BAD07475), *Zea mays* (NCBI Reference Sequence: NP 001149229). and *Oryza sativa* (GenBank Accession No. BAD82000). The resulting alignment is shown in FIG. 9. FIG. 10 shows a phylogenetic tree indicating the relatedness of nepenthesin proteins between different species. Table 1 shows the pairwise alignment scores between each sequence.

TABLE 1

| Sequence 1 | Sequence 2 | Score |
|---|---|---|
| *N. mirabilis* nepenthesin I | *N. mirabilis* nepenthesin II | 65 |
| *N. mirabilis* nepenthesin I | *N. gracilis* nepenthesin I | 94 |
| *N. mirabilis* nepenthesin I | *N. gracilis* nepenthesin II | 66 |
| *N. mirabilis* nepenthesin I | *N. alata* nepenthesin I | 99 |
| *N. mirabilis* nepenthesin I | *O. sativa* nepenthesin I | 39 |
| *N. mirabilis* nepenthesin I | *O. sativa* nepenthesin II | 24 |
| *N. mirabilis* nepenthesin I | *Z. mays* nepenthesin I | 39 |
| *N. mirabilis* nepenthesin I | *Z. mays* nepenthesin II | 26 |
| *N. mirabilis* nepenthesin II | *N. gracilis* nepenthesin I | 64 |
| *N. mirabilis* nepenthesin II | *N. gracilis* nepenthesin II | 96 |
| *N. mirabilis* nepenthesin II | *N. alata* nepenthesin I | 65 |

TABLE 1-continued

| Sequence 1 | Sequence 2 | Score |
|---|---|---|
| *N. mirabilis* nepenthesin II | *O. sativa* nepenthesin I | 37 |
| *N. mirabilis* nepenthesin II | *O. sativa* nepenthesin II | 24 |
| *N. mirabilis* nepenthesin II | *Z. mays* nepenthesin I | 36 |
| *N. mirabilis* nepenthesin II | *Z. mays* nepenthesin II | 23 |
| *N. gracilis* nepenthesin I | *N. gracilis* nepenthesin II | 66 |
| *N. gracilis* nepenthesin I | *N. alata* nepenthesin I | 94 |
| *N. gracilis* nepenthesin I | *O. sativa* nepenthesin I | 40 |
| *N. gracilis* nepenthesin I | *O. sativa* nepenthesin II | 25 |
| *N. gracilis* nepenthesin I | *Z. mays* nepenthesin I | 38 |
| *N. gracilis* nepenthesin I | *Z. mays* nepenthesin II | 26 |
| *N. gracilis* nepenthesin II | *N. alata* nepenthesin I | 66 |
| *N. gracilis* nepenthesin II | *O. sativa* nepenthesin I | 38 |
| *N. gracilis* nepenthesin II | *O. sativa* nepenthesin II | 27 |
| *N. gracilis* nepenthesin II | *Z. mays* nepenthesin I | 39 |
| *N. gracilis* nepenthesin II | *Z. mays* nepenthesin II | 23 |
| *N. alata* nepenthesin I | *O. sativa* nepenthesin I | 39 |
| *N. alata* nepenthesin I | *O. sativa* nepenthesin II | 25 |
| *N. alata* nepenthesin I | *Z. mays* nepenthesin I | 39 |
| *N. alata* nepenthesin I | *Z. mays* nepenthesin II | 26 |
| *O. sativa* nepenthesin I | *O. sativa* nepenthesin II | 28 |
| *O. sativa* nepenthesin I | *Z. mays* nepenthesin I | 35 |
| *O. sativa* nepenthesin I | *Z. mays* nepenthesin II | 23 |
| *O. sativa* nepenthesin II | *Z. mays* nepenthesin I | 24 |
| *O. sativa* nepenthesin II | *Z. mays* nepenthesin II | 15 |
| *Z. mays* nepenthesin I | *Z. mays* nepenthesin II | 26 |

The data as set forth in the examples above demonstrate that nepenthesin, either as a mixture or purified or recombinant components thereof, efficiently digest gluten, whereas pepsin does not. Accordingly, this invention provides for a method to allow for the digestion of gluten in a protein comprising gluten by use of a mixture of nepenthesin or purified or recombinant components thereof.

Although the foregoing has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A composition for treating or attenuating gluten intolerance comprising:
   (a) an effective amount of nepenthesin, the nepenthesin comprising an amino acid sequence that is at least 85% identical to the amino acid sequence selected from the group consisting of SEQ ID NO: 3, SEQ ID NO: 4, SEQ ID NO: 5, SEQ ID NO: 6, and SEQ ID NO: 7, without a plant signal sequence and having aspartic protease activity; and
   (b) an effective amount of a buffer to maintain the pH of said composition at a pH of 5 or above, wherein said nepenthesin is inactive prior to administration;
   wherein said effective amount of nepenthesin is sufficient to degrade gluten upon oral administration of said solid composition to a patient suffering from gluten intolerance.

2. The composition of claim 1, wherein said effective amount of nepenthesin is between about 1 mg and about 1 g, wherein about refers to a variation of up to ±5%.

3. The composition of claim 1, further comprising at least one additional agent selected from the group consisting of an inhibitor of a transglutaminase, an anti-inflammatory agent, a COX-2 inhibitor, a p38 MAP kinase inhibitor, a mast cell-stabilizing agent, an anti-ulcer agent, an anti-allergy agent, and an anti-TNF-α agent.

4. The composition of claim 1, further comprising at least one additional enzyme selected from the group consisting of a gastric protease, an aspartic protease, and a prolyl endopeptidase.

5. The composition of claim 1, wherein said composition is formulated to release said nepenthesin in a patient's stomach.

6. The composition of claim 2, wherein said effective amount of said nepenthesin is between about 1 mg and about 500 mg.

7. The composition of claim 2, wherein said effective amount of said nepenthesin is between about 1 mg and about 200 mg.

8. The composition of claim 1, wherein the gluten intolerance is celiac disease, wheat allergy, gluten sensitivity, or dermatitis herpetiformis.

9. The composition of claim 1, wherein the nepenthesin comprises an amino acid sequence that is at least 85% identical to the amino acid sequence set forth in SEQ ID NO: 3.

10. The composition of claim 1, wherein the nepenthesin comprises an amino acid sequence that is at least 85% identical to the amino acid sequence set forth in SEQ ID NO: 4.

11. The composition of claim 1, wherein the nepenthesin comprises an amino acid sequence that is at least 85% identical to the amino acid sequence set forth in SEQ ID NO: 5.

12. The composition of claim 1, wherein the nepenthesin comprises an amino acid sequence that is at least 85% identical to the amino acid sequence of set forth in SEQ ID NO: 6.

13. The composition of claim 1, wherein the nepenthesin comprises an amino acid sequence that is at least 85% identical to the amino acid sequence set forth in SEQ ID NO: 7.

14. The composition of claim 1, wherein the nepenthesin comprises an amino acid sequence that is at least 90% identical to the amino acid sequence selected from the group consisting of SEQ ID NO: 3, SEQ ID NO: 4, SEQ ID NO: 5, SEQ ID NO: 6, and SEQ ID NO: 7.

15. The composition of claim 1, wherein the nepenthesin comprises an amino acid sequence that is at least 95% identical to the amino acid sequence selected from the group consisting of SEQ ID NO: 3, SEQ ID NO: 4, SEQ ID NO: 5, SEQ ID NO: 6, and SEQ ID NO: 7.

16. The composition of claim 1, wherein the nepenthesin is recombinant nepenthesin.

17. The composition of claim 1, wherein the nepenthesin comprises the amino acid sequence set forth in SEQ ID NO: 3.

18. The composition of claim 1, wherein the nepenthesin comprises the amino acid sequence set forth in SEQ ID NO: 4.

19. The composition of claim 1, wherein the nepenthesin comprises the amino acid sequence set forth in SEQ ID NO: 5.

20. The composition of claim 1, wherein the nepenthesin comprises the amino acid sequence of set forth in SEQ ID NO: 6.

21. The composition of claim 1, wherein the nepenthesin comprises the amino acid sequence set forth in SEQ ID NO: 7.

* * * * *

SEQUENCE LISTING

<160> NUMBER OF SEQ ID NOS: 11

<210> SEQ ID NO 1
<211> LENGTH: 1234
<212> TYPE: DNA
<213> ORGANISM: Nepenthes gracilis

<400> SEQUENCE: 1

```
acgtcaagaa cagctctcaa tcaccgtcac gaagccaaag taacgggctt tcagataatg      60
cttgaacatg ttgattcggg caaaaactta accaaattcc agctcttaga acgtgctatc     120 gaaagggta gtcgtagatt gcagaggctc gaagccatgt taaatggccc ctccggtgtg     180
gaaacttccg tctacgccgg agatggcgaa tatctgatga acttatcgat tggaactccg     240
gcacaacctt tctccgcaat catggatacc ggtagcgatc ttatctggac gcagtgccag     300
ccttgcactc agtgttttaa tcaatcaacg cccatattta atcctcaagg atcatcctcc     360
ttctccaccc tcccttgctc aagccaactc tgtcaagccc tttcaagccc gacatgctct     420
aataatttct gccaatacac ctacgggtat ggggacgggt ccgaaaccca aggatccatg     480
ggcactgaga ctctcacttt cgggtcggtt tccatcccta atatcacatt cggctgcggg     540
gaaaacaacc aagggtttgg gcaaggaaac ggggcaggct tggttgggat gggtcggggc     600
```

```
cctctgtcgc ttccttctca actcgtcgtg accaaattct cttactgcat gacccccatt    660
ggtagctcaa cccctagcac tcttctattg ggatcactgg ctaattctgt caccgccggt    720
agtcctaata caaccctaat ccaaagctct caaataccaa ctttctatta tattactctc    780
aacgggttga gtgttggttc aactcgcttg cccattgatc cgagtgcttt tgcacttaat    840
agcaataatg aacaggagg gataataata gactctggaa cgacacttac ttacttcgtt    900
aacgcttatc aatctgtaag gcaagagttc atctcccaga ttaatctacc cgtcgtaaat    960
ggttcctcct ccggctttga tctgtgcttc cagacgcctt ctgatccgtc aaacctgcag   1020
atacccacct ttgtgatgca ttttgacggt ggagatttgg agttgcccag tgagaattat   1080
ttcatctccc caagcaacgg gctgatttgc ttggcgatgg ggagttcgtc gcaggggatg   1140 tccattttg ggaatattca gcagcaaaac atgctagtcg tttacgacac cggaaattcg   1200
gtggtttcat tcgcttctgc tcaatgtggt gcgt                               1234
```

<210> SEQ ID NO 2
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Gly Pro Leu Gly Ser Met Glu Arg Lys Ile Ser Arg Ile His Leu Val
1               5                   10                  15

Ser Glu Pro Ser Ile Thr His Phe Leu Gln Val Ser Trp Glu Lys Thr
            20                  25                  30

Leu Glu Ser Gly Phe Val Ile Thr Leu Thr Asp Gly His Ser Ala Trp
        35                  40                  45

Thr Gly Thr Val Ser Glu Ser Glu Ile Ser Gln Glu Ala Asp Asp Met
    50                  55                  60

Ala Met Glu Lys Gly Lys Tyr Val Gly Glu Leu Arg Lys Ala Leu Leu
65                  70                  75                  80

Ser Gly Ala Gly Pro Ala Asp Val Tyr Thr Phe Asn Phe Ser Lys Glu
                85                  90                  95

Ser Cys Tyr Phe Phe Phe Glu Lys Asn Leu Lys Asp Val Ser Phe Arg
            100                 105                 110

Leu Gly Ser Phe Asn Leu Glu Lys Val Glu Asn Pro Ala Glu Val Ile
        115                 120                 125

Arg Glu Leu Ile Cys Tyr Cys Leu Asp Thr Ile Ala Glu Asn Gln Ala
    130                 135                 140

Lys Asn Glu His Leu Gln Lys Glu Asn Glu Arg Leu Leu Arg Asp Trp
145                 150                 155                 160

Asn Asp Val Gln Gly Arg Phe Glu Lys Cys Val Ser Ala Lys Glu Ala
                165                 170                 175

Leu Glu Thr Asp Leu Tyr Lys Arg Phe Ile Leu Val Leu Asn Glu Lys
            180                 185                 190

Lys Thr Lys Ile Arg Ser Leu His Asn Lys Leu Leu Asn Ala Ala Gln
        195                 200                 205

Glu Arg Glu Lys Asp Ile Lys Gln Glu Gly Glu Thr Ala Ile Cys Ser
    210                 215                 220

Glu Met Thr Ala Asp Arg Asp Pro Val Tyr Asp Glu Ser Thr Asp Glu
225                 230                 235                 240
```

```
Glu Ser Glu Asn Gln Thr Asp Leu Ser Gly Leu Ala Ser Ala Ala Val
                245                 250                 255

Ser Lys Asp Asp Ser Ile Ile Ser Ser Leu Asp Val Thr Asp Ile Ala
            260                 265                 270

Pro Ser Arg Lys Arg Arg Gln Arg Met Gln Arg Asn Leu Gly Thr Glu
            275                 280                 285

Pro Lys Met Ala Pro Gln Glu Asn Gln Leu Gln Glu Lys Glu Asn Ser
            290                 295                 300

Arg Pro Asp Ser Ser Leu Pro Glu Thr Ser Lys Lys Glu His Ile Ser
305                 310                 315                 320

Ala Glu Asn Met Ser Leu Glu Thr Leu Arg Asn Ser Ser Pro Glu Asp
                325                 330                 335

Leu Phe Asp Glu Ile
            340

<210> SEQ ID NO 3
<211> LENGTH: 437
<212> TYPE: PRT
<213> ORGANISM: Nepenthes mirabilis

<400> SEQUENCE: 3

Met Ala Ser Ser Leu Tyr Ser Phe Leu Leu Ala Leu Ser Ile Val Tyr
1               5                   10                  15

Ile Phe Val Ala Pro Thr His Ser Thr Ser Arg Thr Ala Leu Asn His
                20                  25                  30

His His Glu Pro Lys Val Ala Gly Phe Gln Ile Met Leu Glu His Val
            35                  40                  45

Asp Ser Gly Lys Asn Leu Thr Lys Phe Glu Leu Leu Glu Arg Ala Val
50                  55                  60

Glu Arg Gly Ser Arg Arg Leu Gln Arg Leu Glu Ala Met Leu Asn Gly
65                  70                  75                  80

Pro Ser Gly Val Glu Thr Pro Val Tyr Ala Gly Asp Gly Glu Tyr Leu
                85                  90                  95

Met Asn Leu Ser Ile Gly Thr Pro Ala Gln Pro Phe Ser Ala Ile Met
                100                 105                 110

Asp Thr Gly Ser Asp Leu Ile Trp Thr Gln Cys Gln Pro Cys Thr Gln
            115                 120                 125

Cys Phe Asn Gln Ser Thr Pro Ile Phe Asn Pro Gln Gly Ser Ser Ser
            130                 135                 140

Phe Ser Thr Leu Pro Cys Ser Ser Gln Leu Cys Gln Ala Leu Gln Ser
145                 150                 155                 160

Pro Thr Cys Ser Asn Asn Ser Cys Gln Tyr Thr Tyr Gly Tyr Gly Asp
                165                 170                 175

Gly Ser Glu Thr Gln Gly Ser Met Gly Thr Glu Thr Leu Thr Phe Gly
                180                 185                 190

Ser Val Ser Ile Pro Asn Ile Thr Phe Gly Cys Gly Glu Asn Asn Gln
            195                 200                 205

Gly Phe Gly Gln Gly Asn Gly Ala Gly Leu Val Gly Met Gly Arg Gly
            210                 215                 220

Pro Leu Ser Leu Pro Ser Gln Leu Asp Val Thr Lys Phe Ser Tyr Cys
225                 230                 235                 240

Met Thr Pro Ile Gly Ser Ser Thr Ser Ser Leu Leu Leu Gly Ser
                245                 250                 255

Leu Ala Asn Ser Val Thr Ala Gly Ser Pro Asn Thr Thr Leu Ile Glu
            260                 265                 270
```

-continued

Ser Ser Gln Ile Pro Thr Phe Tyr Tyr Ile Thr Leu Asn Gly Leu Ser
            275                 280                 285

Val Gly Ser Thr Pro Leu Pro Ile Asp Pro Ser Val Phe Lys Leu Asn
    290                 295                 300

Ser Asn Asn Gly Thr Gly Gly Ile Ile Ile Asp Ser Gly Thr Thr Leu
305                 310                 315                 320

Thr Tyr Phe Ala Asp Asn Ala Tyr Gln Ala Val Arg Gln Ala Phe Ile
                325                 330                 335

Ser Gln Met Asn Leu Ser Val Val Asn Gly Ser Ser Gly Phe Asp
            340                 345                 350

Leu Cys Phe Gln Met Pro Ser Asp Gln Ser Asn Leu Gln Ile Pro Thr
            355                 360                 365

Phe Val Met His Phe Asp Gly Gly Asp Leu Val Leu Pro Ser Glu Asn
    370                 375                 380

Tyr Phe Ile Ser Pro Ser Asn Gly Leu Ile Cys Leu Ala Met Gly Ser
385                 390                 395                 400

Ser Ser Gln Gly Met Ser Ile Phe Gly Asn Ile Gln Gln Gln Asn Leu
                405                 410                 415

Leu Val Val Tyr Asp Thr Gly Asn Ser Val Val Ser Phe Leu Phe Ala
            420                 425                 430

Gln Cys Gly Ala Ser
        435

<210> SEQ ID NO 4
<211> LENGTH: 437
<212> TYPE: PRT
<213> ORGANISM: Nepenthes alata

<400> SEQUENCE: 4

Met Ala Ser Ser Leu Tyr Ser Phe Leu Leu Ala Leu Ser Ile Val Tyr
1               5                   10                  15

Ile Phe Val Ala Pro Thr His Ser Thr Ser Arg Thr Ala Leu Asn His
            20                  25                  30

His His Glu Pro Lys Val Ala Gly Phe Gln Ile Met Leu Glu His Val
        35                  40                  45

Asp Ser Gly Lys Asn Leu Thr Lys Phe Glu Leu Leu Glu Arg Ala Val
    50                  55                  60

Glu Arg Gly Ser Arg Arg Leu Gln Arg Leu Glu Ala Met Leu Asn Gly
65                  70                  75                  80

Pro Ser Gly Val Glu Thr Pro Val Tyr Ala Gly Asp Gly Glu Tyr Leu
                85                  90                  95

Met Asn Leu Ser Ile Gly Thr Pro Ala Gln Pro Phe Ser Ala Ile Met
            100                 105                 110

Asp Thr Gly Ser Asp Leu Ile Trp Thr Gln Cys Gln Pro Cys Thr Gln
        115                 120                 125

Cys Phe Asn Gln Ser Thr Pro Ile Phe Asn Pro Gln Gly Ser Ser Ser
    130                 135                 140

Phe Ser Thr Leu Pro Cys Ser Ser Gln Leu Cys Gln Ala Leu Gln Ser
145                 150                 155                 160

Pro Thr Cys Ser Asn Asn Ser Cys Gln Tyr Thr Tyr Gly Tyr Gly Asp
                165                 170                 175

Gly Ser Glu Thr Gln Gly Ser Met Gly Thr Glu Thr Leu Thr Phe Gly
            180                 185                 190

Ser Val Ser Ile Pro Asn Ile Thr Phe Gly Cys Gly Glu Asn Asn Gln

```
            195                 200                 205
Gly Phe Gln Gly Asn Gly Ala Gly Leu Val Gly Met Gly Arg Gly
    210                 215                 220
Pro Leu Ser Leu Pro Ser Gln Leu Asp Val Thr Lys Phe Ser Tyr Cys
225                 230                 235                 240
Met Thr Pro Ile Gly Ser Asn Ser Ser Thr Leu Leu Leu Gly Ser
                245                 250                 255
Leu Ala Asn Ser Val Thr Ala Gly Ser Pro Asn Thr Thr Leu Ile Gln
            260                 265                 270
Ser Ser Gln Ile Pro Thr Phe Tyr Tyr Ile Thr Leu Asn Gly Leu Ser
            275                 280                 285
Val Gly Ser Thr Pro Leu Pro Ile Asp Pro Ser Val Phe Lys Leu Asn
    290                 295                 300
Ser Asn Asn Gly Thr Gly Gly Ile Ile Ile Asp Ser Gly Thr Thr Leu
305                 310                 315                 320
Thr Tyr Phe Val Asp Asn Ala Tyr Gln Ala Val Arg Gln Ala Phe Ile
                325                 330                 335
Ser Gln Met Asn Leu Ser Val Val Asn Gly Ser Ser Ser Gly Phe Asp
            340                 345                 350
Leu Cys Phe Gln Met Pro Ser Asp Gln Ser Asn Leu Gln Ile Pro Thr
        355                 360                 365
Phe Val Met His Phe Asp Gly Gly Asp Leu Val Leu Pro Ser Glu Asn
    370                 375                 380
Tyr Phe Ile Ser Pro Ser Asn Gly Leu Ile Cys Leu Ala Met Gly Ser
385                 390                 395                 400
Ser Ser Gln Gly Met Ser Ile Phe Gly Asn Ile Gln Gln Asn Leu
                405                 410                 415
Leu Val Val Tyr Asp Thr Gly Asn Ser Val Val Ser Phe Leu Ser Ala
            420                 425                 430
Gln Cys Gly Ala Ser
        435

<210> SEQ ID NO 5
<211> LENGTH: 437
<212> TYPE: PRT
<213> ORGANISM: Nepenthes gracilis

<400> SEQUENCE: 5

Met Ala Ser Ser Leu Tyr Ser Phe Leu Leu Ala Leu Ser Ile Val Tyr
1               5                   10                  15
Ile Phe Val Ala Pro Thr His Ser Thr Ser Arg Thr Ala Leu Asn His
                20                  25                  30
Arg His Glu Ala Lys Val Thr Gly Phe Gln Ile Met Leu Glu His Val
            35                  40                  45
Asp Ser Gly Lys Asn Leu Thr Lys Phe Gln Leu Leu Glu Arg Ala Ile
        50                  55                  60
Glu Arg Gly Ser Arg Arg Leu Gln Arg Leu Glu Ala Met Leu Asn Gly
65                  70                  75                  80
Pro Ser Gly Val Glu Thr Ser Val Tyr Ala Gly Asp Gly Glu Tyr Leu
                85                  90                  95
Met Asn Leu Ser Ile Gly Thr Pro Ala Gln Pro Phe Ser Ala Ile Met
            100                 105                 110
Asp Thr Gly Ser Asp Leu Ile Trp Thr Gln Cys Gln Pro Cys Thr Gln
        115                 120                 125
```

```
Cys Phe Asn Gln Ser Thr Pro Ile Phe Asn Pro Gln Gly Ser Ser Ser
    130                 135                 140

Phe Ser Thr Leu Pro Cys Ser Ser Gln Leu Cys Gln Ala Leu Ser Ser
145                 150                 155                 160

Pro Thr Cys Ser Asn Asn Phe Cys Gln Tyr Thr Tyr Gly Tyr Gly Asp
                165                 170                 175

Gly Ser Glu Thr Gln Gly Ser Met Gly Thr Glu Thr Leu Thr Phe Gly
            180                 185                 190

Ser Val Ser Ile Pro Asn Ile Thr Phe Gly Cys Gly Glu Asn Asn Gln
        195                 200                 205

Gly Phe Gly Gln Gly Asn Gly Ala Gly Leu Val Gly Met Gly Arg Gly
    210                 215                 220

Pro Leu Ser Leu Pro Ser Gln Leu Asp Val Thr Lys Phe Ser Tyr Cys
225                 230                 235                 240

Met Thr Pro Ile Gly Ser Ser Thr Pro Ser Asn Leu Leu Leu Gly Ser
                245                 250                 255

Leu Ala Asn Ser Val Thr Ala Gly Ser Pro Asn Thr Thr Leu Ile Gln
            260                 265                 270

Ser Ser Gln Ile Pro Thr Phe Tyr Tyr Ile Thr Leu Asn Gly Leu Ser
        275                 280                 285

Val Gly Ser Thr Arg Leu Pro Ile Asp Pro Ser Ala Phe Ala Leu Asn
    290                 295                 300

Ser Asn Asn Gly Thr Gly Gly Ile Ile Ile Asp Ser Gly Thr Thr Leu
305                 310                 315                 320

Thr Tyr Phe Val Asn Asn Ala Tyr Gln Ser Val Arg Gln Glu Phe Ile
                325                 330                 335

Ser Gln Ile Asn Leu Pro Val Val Asn Gly Ser Ser Ser Gly Phe Asp
            340                 345                 350

Leu Cys Phe Gln Thr Pro Ser Asp Pro Ser Asn Leu Gln Ile Pro Thr
        355                 360                 365

Phe Val Met His Phe Asp Gly Asp Leu Glu Leu Pro Ser Glu Asn
    370                 375                 380

Tyr Phe Ile Ser Pro Ser Asn Gly Leu Ile Cys Leu Ala Met Gly Ser
385                 390                 395                 400

Ser Ser Gln Gly Met Ser Ile Phe Gly Asn Ile Gln Gln Asn Met
                405                 410                 415

Leu Val Val Tyr Asp Thr Gly Asn Ser Val Val Ser Phe Ala Ser Ala
            420                 425                 430

Gln Cys Gly Ala Ser
        435

<210> SEQ ID NO 6
<211> LENGTH: 437
<212> TYPE: PRT
<213> ORGANISM: Nepenthes mirabilis

<400> SEQUENCE: 6

Met Ala Ser Pro Leu His Ser Val Val Leu Gly Leu Ala Ile Val Ser
1               5                   10                  15

Ala Ile Val Ala Pro Thr Ser Ser Thr Ser Arg Gly Thr Leu Leu His
                20                  25                  30

His Gly Gln Lys Arg Pro Gln Pro Gly Leu Arg Val Val Leu Glu Gln
            35                  40                  45

Val Asp Ser Gly Met Asn Leu Thr Lys Tyr Glu Leu Ile Lys Arg Ala
        50                  55                  60
```

Ile Lys Arg Gly Glu Arg Met Arg Ser Ile Asn Ala Met Leu Gln
65                  70                  75                  80

Ser Ser Ser Gly Ile Glu Thr Pro Val Tyr Ala Gly Ser Gly Glu Tyr
            85                  90                  95

Leu Met Asn Val Ala Ile Gly Thr Pro Ala Ser Ser Leu Ser Ala Ile
                100                 105                 110

Met Asp Thr Gly Ser Asp Leu Ile Trp Thr Gln Cys Glu Pro Cys Thr
            115                 120                 125

Gln Cys Phe Ser Gln Pro Thr Pro Ile Phe Asn Pro Gln Asp Ser Ser
            130                 135                 140

Ser Phe Ser Thr Leu Pro Cys Glu Ser Gln Tyr Cys Asp Leu Pro
145                 150                 155                 160

Ser Glu Ser Cys Tyr Asn Asp Cys Gln Tyr Thr Tyr Gly Tyr Gly Asp
                165                 170                 175

Gly Ser Ser Thr Gln Gly Tyr Met Ala Thr Glu Thr Phe Thr Phe Glu
            180                 185                 190

Thr Ser Ser Val Pro Asn Ile Ala Phe Gly Cys Gly Glu Asp Asn Gln
            195                 200                 205

Gly Phe Gly Gln Gly Asn Gly Ala Gly Leu Ile Gly Met Gly Trp Gly
210                 215                 220

Pro Leu Ser Leu Pro Ser Gln Leu Gly Val Gly Gln Phe Ser Tyr Cys
225                 230                 235                 240

Met Thr Ser Ser Gly Ser Ser Ser Pro Ser Thr Leu Ala Leu Gly Ser
                245                 250                 255

Ala Ala Ser Gly Val Pro Glu Gly Ser Pro Ser Thr Thr Leu Ile His
            260                 265                 270

Ser Ser Leu Asn Pro Thr Tyr Tyr Tyr Ile Thr Leu Gln Gly Ile Thr
            275                 280                 285

Val Gly Gly Asp Asn Leu Gly Ile Pro Ser Ser Thr Phe Gln Leu Gln
290                 295                 300

Asp Asp Gly Thr Gly Gly Met Ile Ile Asp Ser Gly Thr Thr Leu Thr
305                 310                 315                 320

Tyr Leu Pro Gln Asp Ala Tyr Asn Ala Val Ala Gln Ala Phe Thr Asp
                325                 330                 335

Gln Ile Asn Leu Ser Pro Val Asp Glu Ser Ser Gly Leu Ser Thr
            340                 345                 350

Cys Phe Gln Leu Pro Ser Asp Gly Ser Thr Val Gln Val Pro Glu Ile
            355                 360                 365

Ser Met Gln Phe Asp Gly Gly Val Leu Asn Leu Gly Glu Glu Asn Val
            370                 375                 380

Leu Ile Ser Pro Ala Glu Gly Val Ile Cys Leu Ala Met Gly Ser Ser
385                 390                 395                 400

Ser Gln Gln Gly Ile Ser Ile Phe Gly Asn Ile Gln Gln Gln Glu Thr
                405                 410                 415

Gln Val Leu Tyr Asp Leu Gln Asn Leu Ala Val Ser Phe Val Pro Thr
            420                 425                 430

Gln Cys Gly Ala Ser
            435

<210> SEQ ID NO 7
<211> LENGTH: 438
<212> TYPE: PRT
<213> ORGANISM: Nepenthes gracilis

<400> SEQUENCE: 7

Met Ala Ser Pro Leu Tyr Ser Val Val Gly Leu Ala Ile Val Ser
1               5                   10                  15

Ala Ile Val Ala Pro Thr Ser Thr Ser Arg Gly Thr Leu Leu His
                20                  25                  30

His Gly Gln Lys Arg Pro Gln Pro Gly Leu Arg Val Asp Leu Glu Gln
                35                  40                  45

Val Asp Ser Gly Lys Asn Leu Thr Lys Tyr Glu Leu Ile Lys Arg Ala
    50                  55                  60

Ile Lys Arg Gly Glu Arg Arg Met Arg Ser Ile Asn Ala Met Leu Gln
65                  70                  75                  80

Ser Ser Ser Gly Ile Glu Thr Pro Val Tyr Ala Gly Asp Gly Glu Tyr
                    85                  90                  95

Leu Met Asn Val Ala Ile Gly Thr Pro Asp Ser Ser Phe Ser Ala Ile
                100                 105                 110

Met Asp Thr Gly Ser Asp Leu Ile Trp Thr Gln Cys Glu Pro Cys Thr
            115                 120                 125

Gln Cys Phe Ser Gln Pro Thr Pro Ile Phe Asn Pro Gln Asp Ser Ser
        130                 135                 140

Ser Phe Ser Thr Leu Pro Cys Glu Ser Gln Tyr Cys Gln Asp Leu Pro
145                 150                 155                 160

Ser Glu Thr Cys Asn Asn Asn Glu Cys Gln Tyr Thr Tyr Gly Tyr Gly
                165                 170                 175

Asp Gly Ser Thr Thr Gln Gly Tyr Met Ala Thr Glu Thr Phe Thr Phe
            180                 185                 190

Glu Thr Ser Ser Val Pro Asn Ile Ala Phe Gly Cys Gly Glu Asp Asn
        195                 200                 205

Gln Gly Phe Gly Gln Gly Asn Gly Ala Gly Leu Ile Gly Met Gly Trp
    210                 215                 220

Gly Pro Leu Ser Leu Pro Ser Gln Leu Gly Val Gly Gln Phe Ser Tyr
225                 230                 235                 240

Cys Met Thr Ser Tyr Gly Ser Ser Pro Ser Thr Leu Ala Leu Gly
                245                 250                 255

Ser Ala Ala Ser Gly Val Pro Glu Gly Ser Pro Ser Thr Thr Leu Ile
            260                 265                 270

His Ser Ser Leu Asn Pro Thr Tyr Tyr Ile Thr Leu Gln Gly Ile
        275                 280                 285

Thr Val Gly Gly Asp Asn Leu Gly Ile Pro Ser Ser Thr Phe Gln Leu
    290                 295                 300

Gln Asp Asp Gly Thr Gly Gly Met Ile Ile Asp Ser Gly Thr Thr Leu
305                 310                 315                 320

Thr Tyr Leu Pro Gln Asp Ala Tyr Asn Ala Val Ala Gln Ala Phe Thr
                325                 330                 335

Asp Gln Ile Asn Leu Pro Thr Val Asp Glu Ser Ser Ser Gly Leu Ser
            340                 345                 350

Thr Cys Phe Gln Gln Pro Ser Asp Gly Ser Thr Val Gln Val Pro Glu
        355                 360                 365

Ile Ser Met Gln Phe Asp Gly Gly Val Leu Asn Leu Gly Glu Gln Asn
    370                 375                 380

Ile Leu Ile Ser Pro Ala Glu Gly Val Ile Cys Leu Ala Met Gly Ser
385                 390                 395                 400

Ser Ser Gln Leu Gly Ile Ser Ile Phe Gly Asn Ile Gln Gln Gln Glu
                405                 410                 415

-continued

```
Thr Gln Val Leu Tyr Asp Leu Gln Asn Leu Ala Val Ser Phe Val Pro
            420                 425                 430
Thr Gln Cys Gly Ala Ser
        435

<210> SEQ ID NO 8
<211> LENGTH: 472
<212> TYPE: PRT
<213> ORGANISM: Zea mays

<400> SEQUENCE: 8

Met Ala Phe His Ser Cys Thr Ile Ile Pro Ala Ser His His Ser Ser
1               5                   10                  15

Met Ser Ser Ser Thr Ser Gln Met Ala Ser Leu Ala Val Leu Val Phe
            20                  25                  30

Leu Val Val Cys Ala Thr Leu Ala Ser Gly Ala Ala Ser Val Arg Val
        35                  40                  45

Gly Leu Thr Arg Ile His Ser Asp Pro Asp Thr Thr Ala Pro Gln Phe
    50                  55                  60

Val Arg Asp Ala Leu Arg Arg Asp Met His Arg Gln Arg Ser Arg Ser
65                  70                  75                  80

Phe Gly Arg Asp Arg Asp Arg Glu Leu Ala Glu Ser Asp Gly Arg Thr
                85                  90                  95

Ser Thr Thr Val Ser Ala Arg Thr Arg Lys Asp Leu Pro Asn Gly Gly
            100                 105                 110

Glu Tyr Leu Met Thr Leu Ala Ile Gly Thr Pro Pro Leu Pro Tyr Ala
        115                 120                 125

Ala Val Ala Asp Thr Gly Ser Asp Leu Ile Trp Thr Gln Cys Ala Pro
    130                 135                 140

Cys Gly Thr Gln Cys Phe Glu Gln Pro Ala Pro Leu Tyr Asn Pro Ala
145                 150                 155                 160

Ser Ser Thr Thr Phe Ser Val Leu Pro Cys Asn Ser Ser Leu Ser Met
                165                 170                 175

Cys Ala Gly Ala Leu Ala Gly Ala Ala Pro Pro Gly Cys Ala Cys
            180                 185                 190

Met Tyr Tyr Gln Thr Tyr Gly Thr Gly Trp Thr Ala Gly Val Gln Gly
        195                 200                 205

Ser Glu Thr Phe Thr Phe Gly Ser Ser Ala Ala Asp Gln Ala Arg Val
    210                 215                 220

Pro Gly Val Ala Phe Gly Cys Ser Asn Ala Ser Ser Asp Trp Asn
225                 230                 235                 240

Gly Ser Ala Gly Leu Val Gly Leu Gly Arg Gly Ser Leu Ser Leu Val
                245                 250                 255

Ser Gln Leu Gly Ala Gly Arg Phe Ser Tyr Cys Leu Thr Pro Phe Gln
            260                 265                 270

Asp Thr Asn Ser Thr Ser Thr Leu Leu Leu Gly Pro Ser Ala Ala Leu
        275                 280                 285

Asn Gly Thr Gly Val Arg Ser Thr Pro Phe Val Ala Ser Pro Ala Arg
    290                 295                 300

Ala Pro Met Ser Thr Tyr Tyr Tyr Leu Asn Leu Thr Gly Ile Ser Leu
305                 310                 315                 320

Gly Ala Lys Ala Leu Pro Ile Ser Pro Gly Ala Phe Ser Leu Lys Pro
                325                 330                 335

Asp Gly Thr Gly Gly Leu Ile Ile Asp Ser Gly Thr Thr Ile Thr Ser
```

```
                340             345                 350
Leu Ala Asn Ala Ala Tyr Gln Gln Val Arg Ala Val Lys Ser Gln
            355                 360             365

Leu Val Thr Thr Leu Pro Thr Val Asp Gly Ser Asp Ser Thr Gly Leu
        370             375             380

Asp Leu Cys Phe Ala Leu Pro Ala Pro Thr Ser Ala Pro Pro Ala Val
385                 390             395                 400

Leu Pro Ser Met Thr Leu His Phe Asp Gly Ala Asp Met Val Leu Pro
                405             410             415

Ala Asp Ser Tyr Met Ile Ser Gly Ser Gly Val Trp Cys Leu Ala Met
            420             425             430

Arg Asn Gln Thr Asp Gly Ala Met Ser Thr Phe Gly Asn Tyr Gln Gln
        435             440             445

Gln Asn Met His Ile Leu Tyr Asp Val Arg Glu Glu Thr Leu Ser Phe
    450             455             460

Ala Pro Ala Lys Cys Ser Thr Leu
465             470
```

<210> SEQ ID NO 9
<211> LENGTH: 453
<212> TYPE: PRT
<213> ORGANISM: Oryza sativa

<400> SEQUENCE: 9

```
Met Arg Gly Val Ser Val Val Leu Val Leu Ile Ala Cys Trp Leu Cys
1               5                   10                  15

Gly Cys Pro Val Ala Gly Glu Ala Ala Phe Ala Gly Asp Ile Arg Val
            20                  25                  30

Asp Leu Thr His Val Asp Ala Gly Lys Glu Leu Pro Lys Arg Glu Leu
        35                  40                  45

Ile Arg Arg Ala Met Gln Arg Ser Lys Ala Arg Ala Ala Leu Ser
    50                  55                  60

Val Val Arg Asn Gly Gly Gly Phe Tyr Gly Ser Ile Ala Gln Ala Arg
65                  70                  75                  80

Glu Arg Glu Arg Glu Pro Gly Met Ala Val Arg Ala Ser Gly Asp Leu
                85                  90                  95

Glu Tyr Val Leu Asp Leu Ala Val Gly Thr Pro Pro Gln Pro Ile Thr
            100                 105                 110

Ala Leu Leu Asp Thr Gly Ser Asp Leu Ile Trp Thr Gln Cys Asp Thr
        115                 120                 125

Cys Thr Ala Cys Leu Arg Gln Pro Asp Pro Leu Phe Ser Pro Arg Met
    130                 135                 140

Ser Ser Tyr Glu Pro Met Arg Cys Ala Gly Gln Leu Cys Gly Asp
145                 150                 155                 160

Ile Leu His His Ser Cys Val Arg Pro Asp Thr Cys Thr Tyr Arg Tyr
                165                 170                 175

Ser Tyr Gly Asp Gly Thr Thr Thr Leu Gly Tyr Tyr Ala Thr Glu Arg
            180                 185                 190

Phe Thr Phe Ala Ser Ser Ser Gly Glu Thr Gln Ser Val Pro Leu Gly
        195                 200                 205

Phe Gly Cys Gly Thr Met Asn Val Gly Ser Leu Asn Asn Ala Ser Gly
    210                 215                 220

Ile Val Gly Phe Gly Arg Asp Pro Leu Ser Leu Val Ser Gln Leu Ser
225                 230                 235                 240
```

Ile Arg Arg Phe Ser Tyr Cys Leu Thr Pro Tyr Ala Ser Ser Arg Lys
            245                 250                 255

Ser Thr Leu Gln Phe Gly Ser Leu Ala Asp Val Gly Leu Tyr Asp Asp
        260                 265                 270

Ala Thr Gly Pro Val Gln Thr Thr Pro Ile Leu Gln Ser Ala Gln Asn
    275                 280                 285

Pro Thr Phe Tyr Tyr Val Ala Phe Thr Gly Val Thr Val Gly Ala Arg
290                 295                 300

Arg Leu Arg Ile Pro Ala Ser Ala Phe Ala Leu Arg Pro Asp Gly Ser
305                 310                 315                 320

Gly Gly Val Ile Ile Asp Ser Gly Thr Ala Leu Thr Leu Phe Pro Val
            325                 330                 335

Ala Val Leu Ala Glu Val Val Arg Ala Phe Arg Ser Gln Leu Arg Leu
        340                 345                 350

Pro Phe Ala Asn Gly Ser Ser Pro Asp Asp Gly Val Cys Phe Ala Ala
    355                 360                 365

Pro Ala Val Ala Ala Gly Gly Arg Met Ala Arg Gln Val Ala Val
370                 375                 380

Pro Arg Met Val Phe His Phe Gln Gly Ala Asp Leu Asp Leu Pro Arg
385                 390                 395                 400

Glu Asn Tyr Val Leu Glu Asp His Arg Arg Gly His Leu Cys Val Leu
            405                 410                 415

Leu Gly Asp Ser Gly Asp Asp Gly Ala Thr Ile Gly Asn Phe Val Gln
        420                 425                 430

Gln Asp Met Arg Val Val Tyr Asp Leu Glu Arg Glu Thr Leu Ser Phe
    435                 440                 445

Ala Pro Val Glu Cys
    450

<210> SEQ ID NO 10
<211> LENGTH: 486
<212> TYPE: PRT
<213> ORGANISM: Oryza sativa

<400> SEQUENCE: 10

Met Ala Asp Arg Ile Thr Val Leu Ala Ile Ala Leu Leu Val Leu Ile
1               5                   10                  15

Leu Ser Pro Gln Met Ala Val Gln Gly Lys Pro Ala Ala Gly Asn Thr
            20                  25                  30

Ala Ser Pro Arg Pro Lys Gln Gln Gln Leu Gly Asn Phe Phe Lys Lys
        35                  40                  45

His Gly Ser Asp Ile Ala Gly Leu Phe Pro Arg His Arg Asn Gly Gly
    50                  55                  60

Ser Ser Gly Ser Tyr Ser Gly Gln Ala Val Pro Ala Asp Gly Gly Glu
65                  70                  75                  80

Asn Gly Gly Gly Gly Gln Ser Gln Asp Pro Ala Thr Asn Thr Gly Met
            85                  90                  95

Tyr Val Leu Ser Phe Ser Val Gly Thr Pro Pro Gln Val Val Thr Gly
            100                 105                 110

Val Leu Asp Ile Thr Ser Asp Phe Val Trp Met Gln Cys Ser Ala Cys
        115                 120                 125

Ala Thr Cys Gly Ala Asp Ala Pro Ala Ala Thr Ser Ala Pro Pro Phe
    130                 135                 140

Tyr Ala Phe Leu Ser Ser Thr Ile Arg Glu Val Arg Cys Ala Asn Arg
145                 150                 155                 160

```
Gly Cys Gln Arg Leu Val Pro Gln Thr Cys Ser Ala Asp Asp Ser Pro
            165                 170                 175

Cys Gly Tyr Ser Tyr Val Tyr Gly Gly Ala Ala Asn Thr Thr Ala
        180                 185                 190

Gly Leu Leu Ala Val Asp Ala Phe Ala Phe Ala Thr Val Arg Ala Asp
            195                 200                 205

Gly Val Ile Phe Gly Cys Ala Val Ala Thr Glu Gly Asp Ile Gly Gly
        210                 215                 220

Val Ile Gly Leu Gly Arg Gly Glu Leu Ser Pro Val Ser Gln Leu Gln
225                 230                 235                 240

Ile Gly Arg Phe Ser Tyr Tyr Leu Ala Pro Asp Ala Val Asp Val
            245                 250                 255

Gly Ser Phe Ile Leu Phe Leu Asp Asp Ala Lys Pro Arg Thr Ser Arg
            260                 265                 270

Ala Val Ser Thr Pro Leu Val Ala Ser Arg Ala Ser Arg Ser Leu Tyr
        275                 280                 285

Tyr Val Glu Leu Ala Gly Ile Arg Val Asp Gly Glu Asp Leu Ala Ile
        290                 295                 300

Pro Arg Gly Thr Phe Asp Leu Gln Ala Asp Gly Ser Gly Val Val
305                 310                 315                 320

Leu Ser Ile Thr Ile Pro Val Thr Phe Leu Asp Ala Gly Ala Tyr Lys
            325                 330                 335

Val Val Arg Gln Ala Met Ala Ser Lys Ile Glu Leu Arg Ala Ala Asp
            340                 345                 350

Gly Ser Glu Leu Gly Leu Asp Leu Cys Tyr Thr Ser Glu Ser Leu Ala
        355                 360                 365

Thr Ala Lys Val Pro Ser Met Ala Leu Val Phe Ala Gly Gly Ala Val
    370                 375                 380

Met Glu Leu Glu Met Gly Asn Tyr Phe Tyr Met Asp Ser Thr Thr Gly
385                 390                 395                 400

Leu Glu Cys Leu Thr Ile Leu Pro Ser Pro Ala Gly Asp Gly Ser Leu
            405                 410                 415

Leu Gly Ser Leu Ile Gln Val Gly Thr His Met Ile Tyr Asp Ile Ser
            420                 425                 430

Gly Ser Arg Leu Val Phe Glu Ser Leu Glu Gln Ala Pro Pro Pro
        435                 440                 445

Ser Gly Ser Ser Arg Gln Ser Ser Arg Arg Ser Ser Ser Ala Pro
    450                 455                 460

Pro Pro Leu Thr Ser Pro Ala Val Val Val Ile His Leu Met Leu Val
465                 470                 475                 480

Val Val Tyr Met Phe Leu
            485
```

<210> SEQ ID NO 11
<211> LENGTH: 471
<212> TYPE: PRT
<213> ORGANISM: Zea mays

<400> SEQUENCE: 11

```
Met Ala Met Met Ala Cys Asn Asn Thr Arg Pro Arg Lys Leu Ser Leu
1               5                   10                  15

Pro Cys Arg Thr Arg Thr Phe Gln Ala Leu Ile Leu Ser Thr Ala Val
            20                  25                  30

Phe Leu Ala Ala Ser Thr Ala Val Val Val Gly Lys Glu Pro Gln Pro
```

```
            35                  40                  45
Pro Ser Ser Gly Gly Gly Cys His Tyr Arg Phe Glu Leu Thr His
 50                  55                  60

Val Asp Ala Asn Leu Asn Leu Thr Ser Asp Glu Leu Met Arg Arg Ala
 65                  70                  75                  80

Tyr Asp Arg Ser Arg Leu Arg Ala Ala Ser Leu Ala Ala Tyr Ser Asp
                 85                  90                  95

Gly Arg His Glu Gly Arg Val Ser Ile Pro Asp Ala Ser Tyr Ile Ile
                100                 105                 110

Thr Phe Tyr Leu Gly Asn Gln Arg Pro Glu Asp Asn Ile Ser Ala Val
                115                 120                 125

Val Asp Thr Gly Ser Asp Ile Phe Trp Thr Thr Glu Lys Glu Cys Ser
130                 135                 140

Arg Ser Lys Thr Arg Ser Met Leu Pro Cys Cys Ser Pro Lys Cys Glu
145                 150                 155                 160

Gln Arg Ala Ser Cys Gly Cys Gly Arg Ser Glu Leu Lys Ala Glu Ala
                165                 170                 175

Glu Lys Glu Thr Lys Cys Thr Tyr Ala Ile Ile Tyr Gly Gly Asn Ala
                180                 185                 190

Asn Asp Ser Thr Ala Gly Val Met Tyr Glu Asp Lys Leu Thr Ile Val
                195                 200                 205

Ala Val Ala Ser Lys Ala Val Pro Ser Ser Gln Ser Phe Lys Glu Val
210                 215                 220

Ala Ile Gly Cys Ser Thr Ser Ala Thr Leu Lys Phe Lys Asp Pro Ser
225                 230                 235                 240

Ile Lys Gly Val Phe Gly Leu Gly Arg Ser Ala Thr Ser Leu Pro Arg
                245                 250                 255

Gln Leu Asn Phe Ser Lys Phe Ser Tyr Cys Leu Ser Ser Tyr Gln Glu
                260                 265                 270

Pro Asp Leu Pro Ser Tyr Leu Leu Leu Thr Ala Ala Pro Asp Met Ala
                275                 280                 285

Thr Gly Ala Val Gly Gly Ala Ala Val Ala Thr Thr Ala Leu Gln
290                 295                 300

Pro Asn Ser Asp Tyr Lys Thr Leu Tyr Phe Val His Leu Gln Asn Ile
305                 310                 315                 320

Ser Ile Gly Gly Thr Arg Phe Pro Ala Val Ser Thr Lys Ser Gly Gly
                325                 330                 335

Asn Met Phe Val Asp Thr Gly Ala Ser Phe Thr Arg Leu Glu Gly Thr
                340                 345                 350

Val Phe Ala Lys Leu Val Thr Glu Leu Asp Arg Ile Met Lys Glu Arg
                355                 360                 365

Lys Tyr Val Lys Glu Gln Pro Gly Arg Asn Asn Gly Gln Ile Cys Tyr
                370                 375                 380

Ser Pro Pro Ser Thr Ala Ala Asp Glu Ser Ser Lys Leu Pro Asp Met
385                 390                 395                 400

Val Leu His Phe Ala Asp Ser Ala Asn Met Val Leu Pro Trp Asp Ser
                405                 410                 415

Tyr Leu Trp Lys Thr Thr Ser Lys Leu Cys Leu Ala Ile Tyr Lys Ser
                420                 425                 430

Asn Ile Lys Gly Gly Ile Ser Val Leu Gly Asn Phe Gln Met Gln Asn
                435                 440                 445
```

-continued

```
Thr His Met Leu Leu Asp Thr Gly Asn Glu Lys Leu Ser Phe Val Arg
    450                 455                 460

Ala Asp Cys Ser Lys Val Ile
465                 470
```